United States Patent
Kirmess et al.

(10) Patent No.: US 10,976,323 B2
(45) Date of Patent: Apr. 13, 2021

(54) METHODS FOR MEASURING CONCENTRATIONS OF BIOMOLECULES IN BIOFLUIDS

(71) Applicant: C2N DIAGNOSTICS LLC, Saint Louis, MS (US)

(72) Inventors: Kristopher Michael Kirmess, St. Louis, MO (US); Kevin Edward Yarasheski, St. Louis, MO (US); Matthew R. Meyer, Chesterfield, MO (US)

(73) Assignee: C2N Diagnostics LLC, Saint Louis, MO (US)

( * ) Notice: Subject to any disclaimer, the term of this patent is extended or adjusted under 35 U.S.C. 154(b) by 191 days.

(21) Appl. No.: 15/893,437

(22) Filed: Feb. 9, 2018

(65) Prior Publication Data

US 2019/0086422 A1    Mar. 21, 2019

Related U.S. Application Data

(60) Provisional application No. 62/500,344, filed on May 2, 2017, provisional application No. 62/473,212, filed
(Continued)

(51) Int. Cl.
*G01N 33/68* (2006.01)
*G01N 33/60* (2006.01)
(Continued)

(52) U.S. Cl.
CPC ....... *G01N 33/6848* (2013.01); *C12N 9/6427* (2013.01); *C12Q 1/00* (2013.01);
(Continued)

(58) Field of Classification Search
CPC .... G01N 33/6848; G01N 33/48; G01N 33/60; G01N 33/6896; G01N 2458/15;
(Continued)

(56) References Cited

U.S. PATENT DOCUMENTS 5,922,551 A  *  7/1999  Durbin ............. G01N 33/54346
                                                    435/13
2009/0142766 A1 * 6/2009 Holtzman .......... G01N 33/6896
                                                    435/6.16
(Continued)

FOREIGN PATENT DOCUMENTS

WO    WO-2017053739 A1 *  3/2017  ......... G01N 33/6896

OTHER PUBLICATIONS

Bros—Antibody free quantification of seven tau peptides in human CSF using targeted mass spectrometry—Fontiers in Neuroscience—2015 (Year: 2015).*
(Continued)

*Primary Examiner* — Benjamin R Whatley
*Assistant Examiner* — Jean Caraballo-Lean
(74) *Attorney, Agent, or Firm* — DLA Piper LLP (US)

(57) ABSTRACT

The present invention provides methods for measuring the absolute concentration of Tau, and other protein, peptide fragments and proteoforms in CSF and plasma samples collected from a subject. Such biomolecules may be implicated in one or more neurological and neurodegenerative diseases or disorders. Also provided is a method for determining whether a therapeutic agent affects the CSF or plasma concentration of a central nervous system derived biomolecule. Also provided are kits for performing the methods of the invention.

8 Claims, 7 Drawing Sheets

Specification includes a Sequence Listing.

TAU IP-MS WORKFLOW

Related U.S. Application Data on Mar. 17, 2017, provisional application No. 62/457,715, filed on Feb. 10, 2017.

(51) Int. Cl.
*C12N 9/76* (2006.01)
*G01N 33/48* (2006.01)
*C12Q 1/00* (2006.01)

(52) U.S. Cl.
CPC ............. *G01N 33/48* (2013.01); *G01N 33/60* (2013.01); *G01N 33/6896* (2013.01); *G01N 2333/4709* (2013.01); *G01N 2458/15* (2013.01); *G01N 2560/00* (2013.01); *G01N 2800/2821* (2013.01)

(58) Field of Classification Search
CPC ... G01N 2333/4709; G01N 2800/2821; G01N 2560/00; C12Q 1/00; C12N 9/6427
See application file for complete search history.

(56) References Cited

U.S. PATENT DOCUMENTS

| | | |
|---|---|---|
| 2012/0029169 A1 | 2/2012 | Moe |
| 2014/0065636 A1 | 3/2014 | West et al. |
| 2015/0253341 A1* | 9/2015 | McAvoy ................ C07K 16/18 435/7.1 |
| 2016/0139142 A1 | 5/2016 | Bateman et al. |
| 2016/0238619 A1 | 8/2016 | West et al. |
| 2016/0347804 A1* | 12/2016 | Griswold-Prenner ....................... A61K 39/0007 |

OTHER PUBLICATIONS

Barthelemy et al.: "*Tau Protein Quantification in Human Cerebrospinal Fluid by Targeted Mass Spectrometry at High Sequence Coverage Provides Insights into Its Primary Structure Heterogeneity*"; Journal of Proteome Research, Jan. 7, 2016, vol. 15, Iss. 2, pp. 667-676.

International Search Report dated May 4, 2018, regarding PCT/US2018/017691.

* cited by examiner

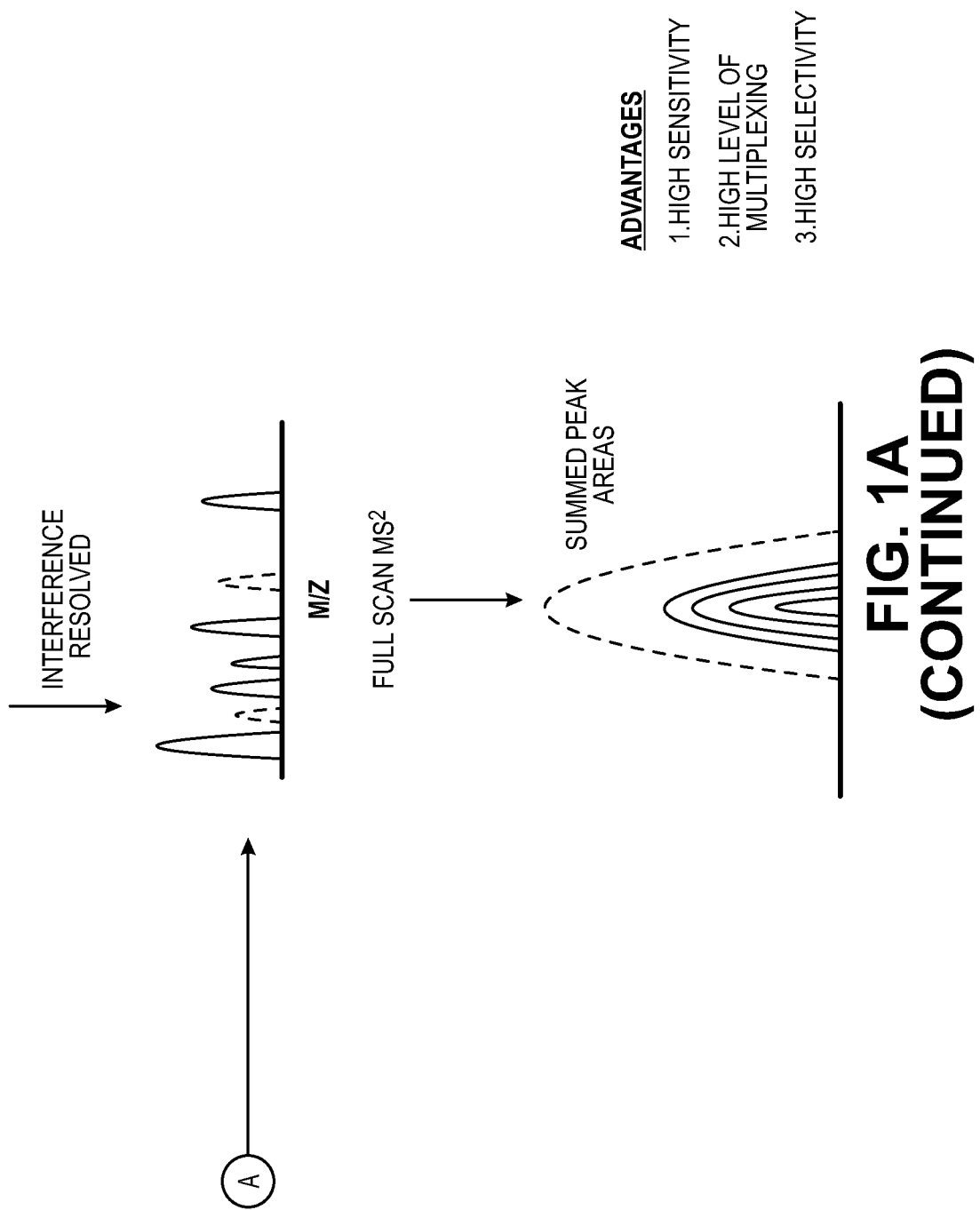

METHODS FOR MEASURING CONCENTRATIONS OF BIOMOLECULES IN BIOFLUIDS

CROSS-REFERENCE TO RELATED APPLICATIONS

This application claims benefit of priority under 35 U.S.C. § 119(e) of U.S. Ser. No. 62/457,715, filed Feb. 10, 2017, of U.S. Ser. No. 62/473,212, filed Mar. 17, 2017 and U.S. Ser. No. 62/500,344, filed May 2, 2017, the entire contents of which are all incorporated herein by reference in its entirety.

INCORPORATION OF SEQUENCE LISTING

The material in the accompanying sequence listing is hereby incorporated by reference into this application. The accompanying sequence listing text file, name C2N1140_3WO_Sequence_Listing, was created on Feb. 9, 2018, and is 36 kb. The file can be assessed using Microsoft Word on a computer that uses Windows OS.

BACKGROUND OF THE INVENTION

Field of the Invention

The invention relates generally to analytical methods for the diagnosis and treatment of neurological and neurodegenerative diseases, disorders, and associated processes.

Background Information

Alzheimer's Disease (AD) is the most common cause of dementia and is an increasing public health problem. It is currently estimated to afflict 5 million people in the United States, with an expected increase to 13 million by the year 2050 (Herbert et al, 2001, *Alzheimer Dis. Assoc. Disord.* 15(4): 169-173). AD, like other central nervous system (CNS) degenerative diseases, is characterized by disturbances in protein production, accumulation, and clearance. In AD, dysregulation in the metabolism of the protein, amyloid-beta (Aβ), is indicated by a massive buildup of this protein in the form of amyloid plaques in the brains of those with the disease. In addition, the protein Tau builds up in the brain in the form of Tau tangles. AD leads to loss of memory, cognitive function, and ultimately independence and death. The disease takes a heavy personal and financial toll on the patient, the family, and society. Because of the severity and increasing prevalence of this disease in the population, it is urgent that better diagnostics and treatments be developed.

Currently, there are some medications that modify symptoms, however, there are no disease-modifying treatments. Disease-modifying treatments will likely be most effective when given before the onset of irreversible brain damage. However, by the time clinical diagnosis of AD is made, extensive neuronal loss has already occurred (Price et al. 2001, *Arch Neurol.* 58(9): 1395-1402). Therefore, a way to identify those at risk of developing AD would be most helpful in preventing or delaying the onset of AD. Currently, there are no means of identifying the pathophysiologic changes that occur in AD before the onset of clinical symptoms or of effectively measuring the effects of treatments that may prevent the onset or slow the progression of the disease.

A need therefore exists for a sensitive, accurate, and reproducible method for quantifying diagnostic biomolecules in the blood as well as the cerebral spinal fluid (CSF) of humans. Previous technologies used for absolute quantitation include enzyme linked immunosorbent assays (ELISAs), which use antibodies to capture and measure the concentrations. However, ELISAs quantitate total concentration or rely on isoform specific antibodies for quantitation and can, for the most part, be used to measure the concentration of only one species per assay. Antibodies used for ELISA assays must be highly specific for the protein species and the conformations of the proteins they bind and the reliance upon two antibodies binding to the protein of interest can lead to high inter- and intra-assay variability in the reported protein concentrations from ELISA assays. As such, a method is needed for measuring the absolute concentrations of one or more neurodegenerative disorder-specific proteins or protein forms in blood plasma or serum, or CSF obtained from humans, where the proteins or biomolecules are associated with the diagnosis and/or progression of diseases.

SUMMARY OF THE INVENTION

Among the various aspects of the present invention is the provision of a method for calculating the concentration of one or more biomolecules in a subject's sample. The method includes contacting a sample from the subject with a Quantitation Internal Standard, where the Quantitation Internal Standard is a known concentration of a labeled biomolecule of interest. The Quantitation Standard can be contacting the sample from the subject either before isolation of the endogenous biomolecules of interest present in the sample or after isolation of the endogenous biomolecule from the sample. The method further includes isolating the endogenous biomolecule of interest from the plasma, serum, or CSF sample and determining a ratio of labeled Quantitation Internal Standard to unlabeled endogenous biomolecules in the sample, which is thereby used to calculate the concentration of the endogenous biomolecule in the sample. In one embodiment, the method further includes normalizing the calculated concentration to a standard curve, wherein the standard curve is generated by determining two or more ratios of endogenous biomolecules to Quantitation Standard, where the concentration of the endogenous biomolecule is known.

In another aspect, the present invention provides a method of quantifying the concentration of one or more peptide fragments that derive from the endogenous protein or proteoforms of interest and present in the plasma, serum, or CSF of a human. The method further includes obtaining a plasma, serum, or CSF sample or tissue from the subject prior to and/or after the subject has been exposed to any therapeutic intervention (drug, chemical, behavioral) that may change the endogenous protein or peptide fragment or proteoform concentration. The sample is then contacted with a Quantitation Internal Standard, where the Quantitation Internal Standard is a known concentration of a labeled biomolecule. As above, calculating the intervention-induced change in the concentration of the endogenous protein or peptide fragment, or proteoform of interest is determined by the ratio of labeled Quantitation Internal Standard to unlabeled endogenous biomolecules in the sample. Another provision of the process comprises comparing the change in the endogenous protein, peptide fragment, or proteoforms concentration in the subject to a suitable control value or subject, wherein a change from the control value or subject indicates how the therapeutic intervention affects the protein, peptide fragment, or proteoforms concentration in the plasma, serum or CSF of the subject.

In yet another embodiment, the calculated concentrations of endogenous and labeled proteins, peptide fragments, or proteoforms are normalized to each of their individual standard curves, wherein the standard curve is generated by determining the ratio of unlabeled endogenous and labeled biomolecules to Quantitation Internal Standard, where the concentration of unlabeled endogenous and labeled biomolecule is known.

In another aspect, the invention provides a kit for performing the methods of the invention. In one embodiment, a kit is provided for diagnosing and/or monitoring the progression or treatment of a neurological or neurodegenerative disease in a subject. The kit includes a means for obtaining a biological sample at regular time intervals from the subject. In certain embodiments, the kit will also include instructions for processing the biological samples to make them suitable for freezing and shipping to a suitable analytical laboratory. In certain embodiments, the kit will also include instructions for preparing the samples for detecting and determining the ratio of labeled to unlabeled endogenous proteins, peptide fragments, or proteoforms of interest over time and for calculating the concentration of the endogenous proteins, peptide fragments, or proteoforms. In one embodiment, the instructions will disclose methods for comparing the calculated concentration to certain standards and/or controls as disclosed herein.

In some aspects, the Quantitation Internal Standard contains a non-radioactive isotope that is selected from the group consisting of $^2H$, $^{13}C$, $^{15}$, $^{17}O$, $^{18}O$, $^{33}S$, $^{34}S$, and $^{36}S$. In one embodiment, the labeled moiety is uniformly labeled $^{15}N$-Tau with 441 amino acid residues. In some aspects, the endogenous biomolecule may be a protein, peptide fragment, or proteoform present in the central nervous system such as Tau. In aspects of the invention where two or more biomolecules are assayed, the biomolecules may be isoforms of the same protein. As such, in one embodiment, the biomolecule may be one or more of Tau-4R2N, Tau-4R1N, Tau-4R0N, Tau-3R2N, Tau-3R1N, Tau-3R0N.

Other aspects and features of the invention are described in more detail below.

DETAILED DESCRIPTION OF THE INVENTION

Figure 1A:
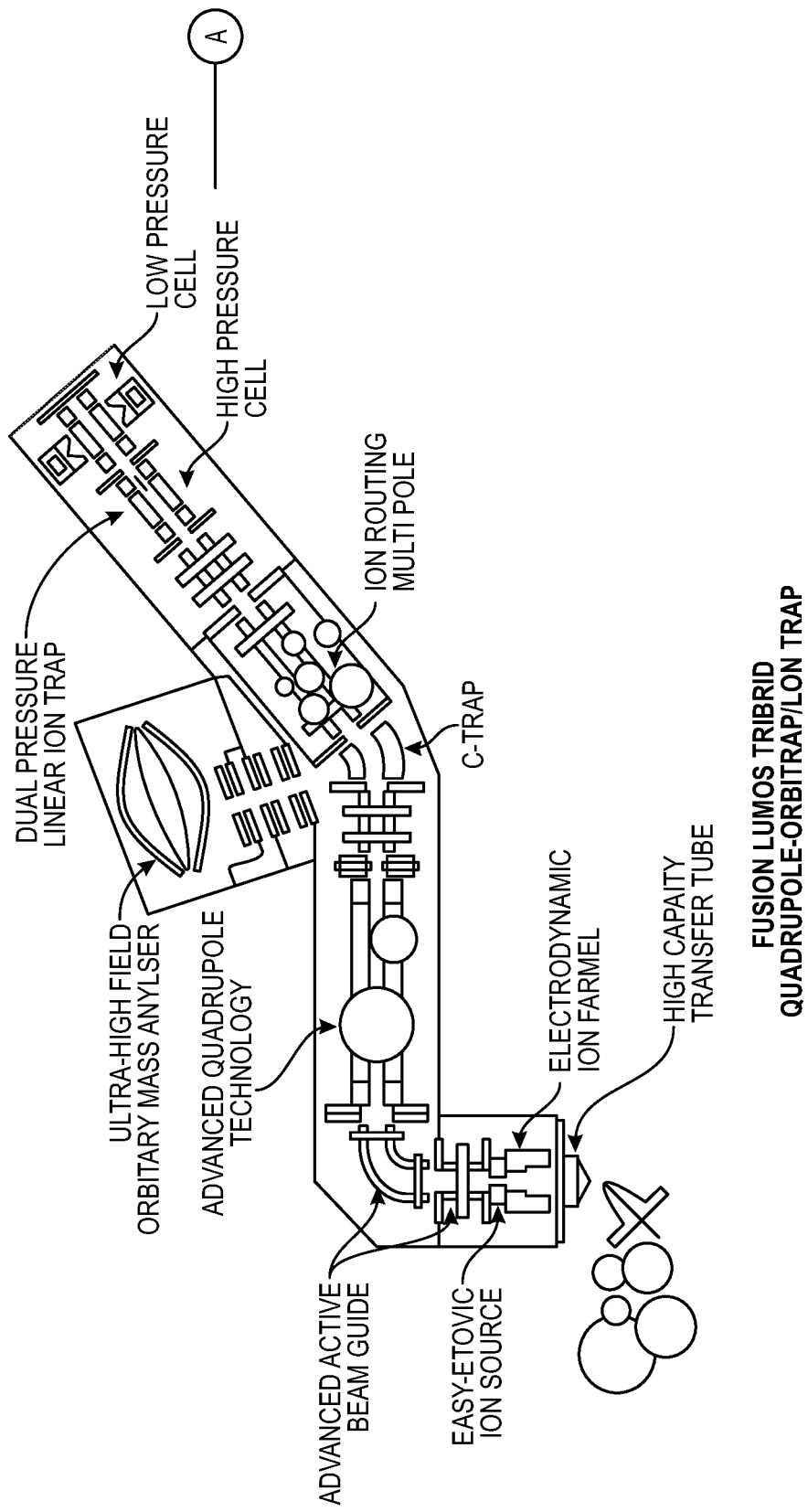
FIG. 1A shows an overview of how $^{15}N$-Tau-441 is used as the Quantitation Internal Standard, added to the biological sample at a known concentration, the Quantitation Internal Standard and endogenous proteins are digested with trypsin, or another proteolytic enzyme, to form peptide fragments that are specific to the protein from which they derive. The mass, amino acid sequence, and relative abundance of the peptides derived from endogenous proteins and $^{15}N$-Tau-441 protein are determined using a mass spectrometer. The concentration of each peptide derived from endogenous Tau is determined by the mass spectrometer signal intensity for each peptide expressed as a ratio to the signal intensity for the corresponding $^{15}N$-labeled peptide derived from $^{15}N$-Tau-441. A series of standards that contain different but known quantities of endogenous Tau and $^{15}N$-Tau-441 and that are processed exactly the same as the biological samples are used to generate a quantitation standard curve. To those persons skilled in the art, FIG. 1B details the mass fragmentation pattern obtained from a select endogenous Tau peptide, the mass fragmentation pattern obtained from the corresponding peptide present in the $^{15}N$-Tau-441 Quantitation Internal Standard, and the relative abundance (Gaussian peaks or signals) obtained by mass spectrometry for several endogenous and $^{15}N$-labeled fragments (y- and a-ions). In this aspect, the mass fragmentation pattern specifically identifies the amino acid sequence for this Tau peptide, and the relative abundance signals for the known concentration of the $^{15}N$-labeled fragments are used to calculate the concentration of the endogenous $^{14}N$-Tau peptide.
Figure 1B:
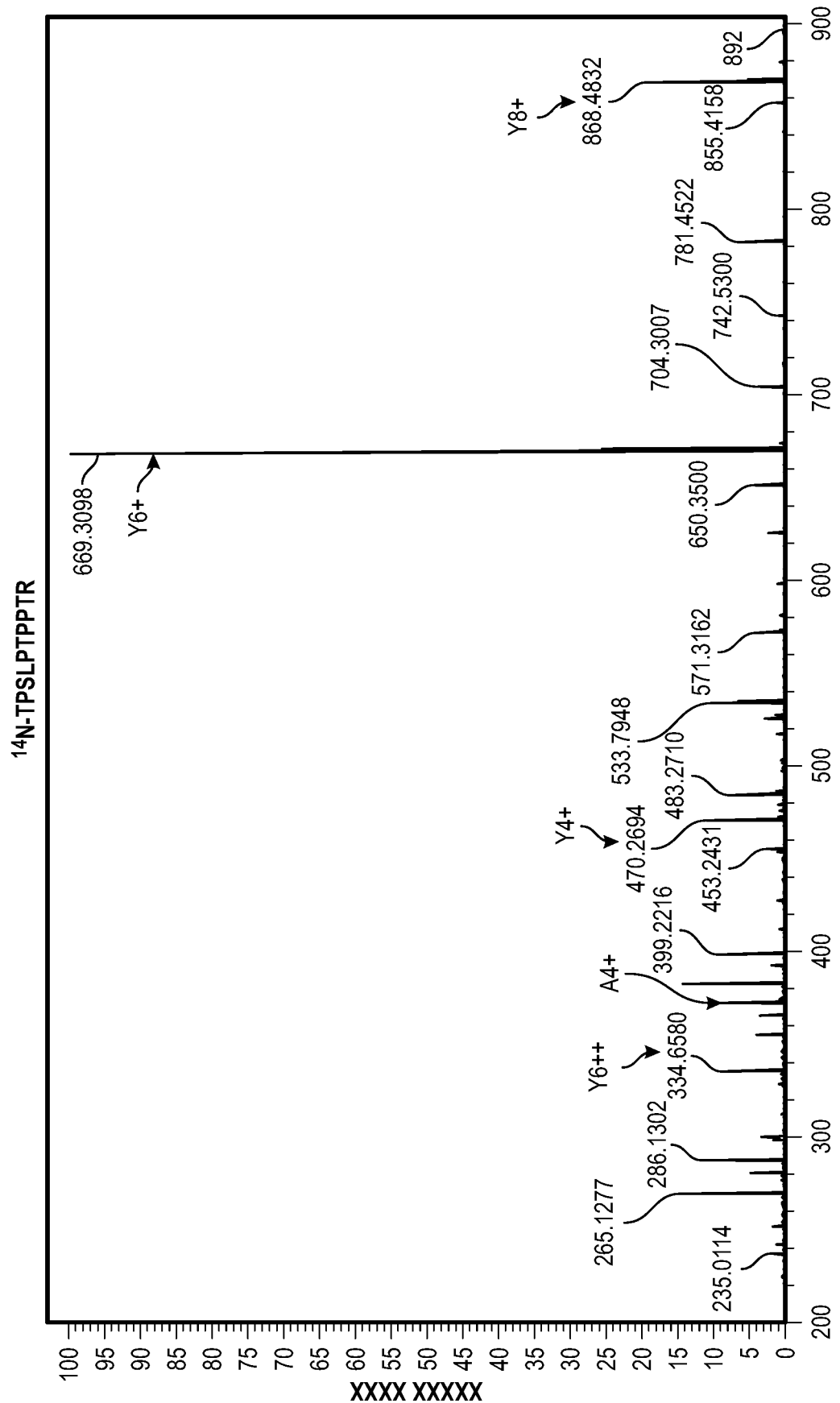
Figure 1B:
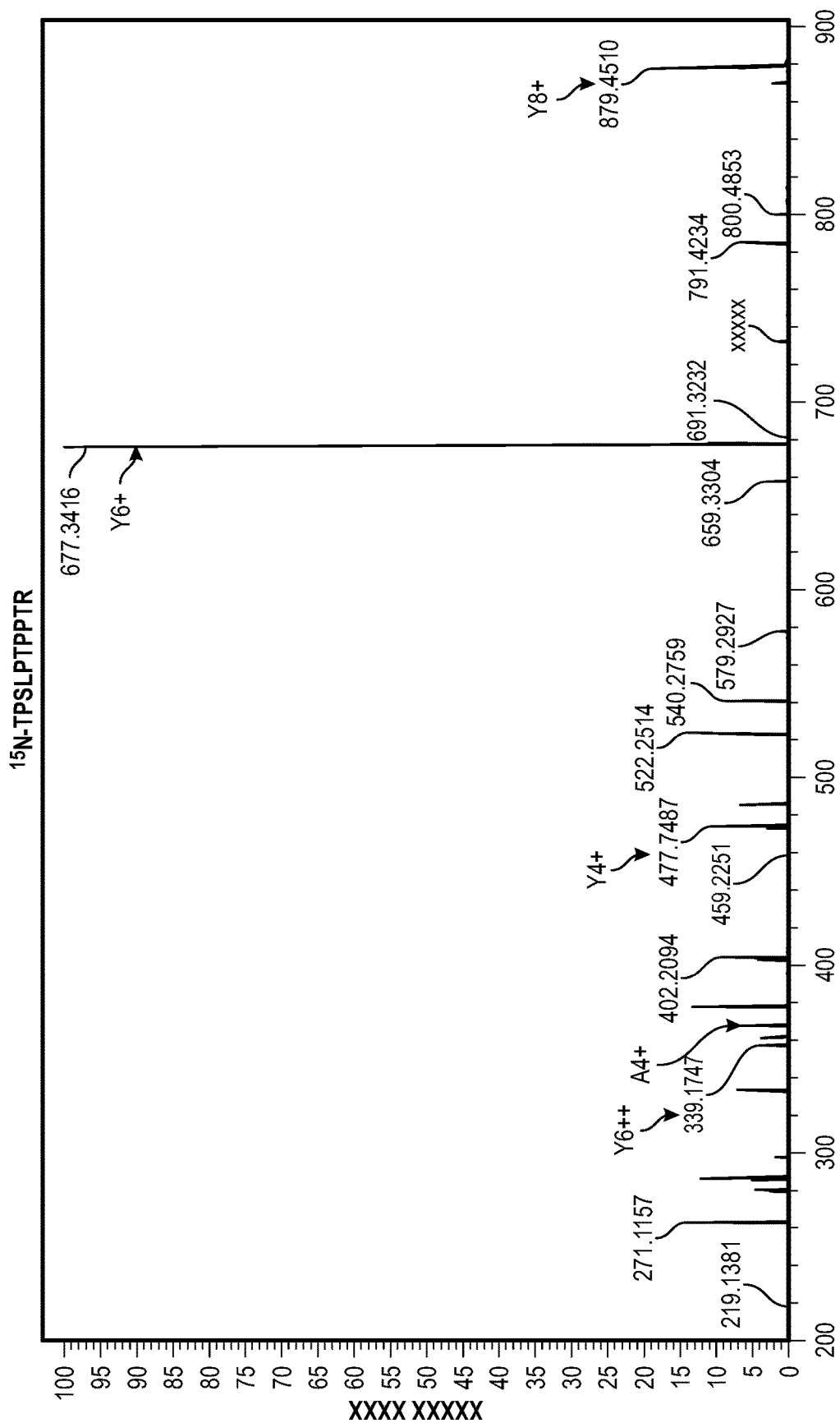
Figure 1B:
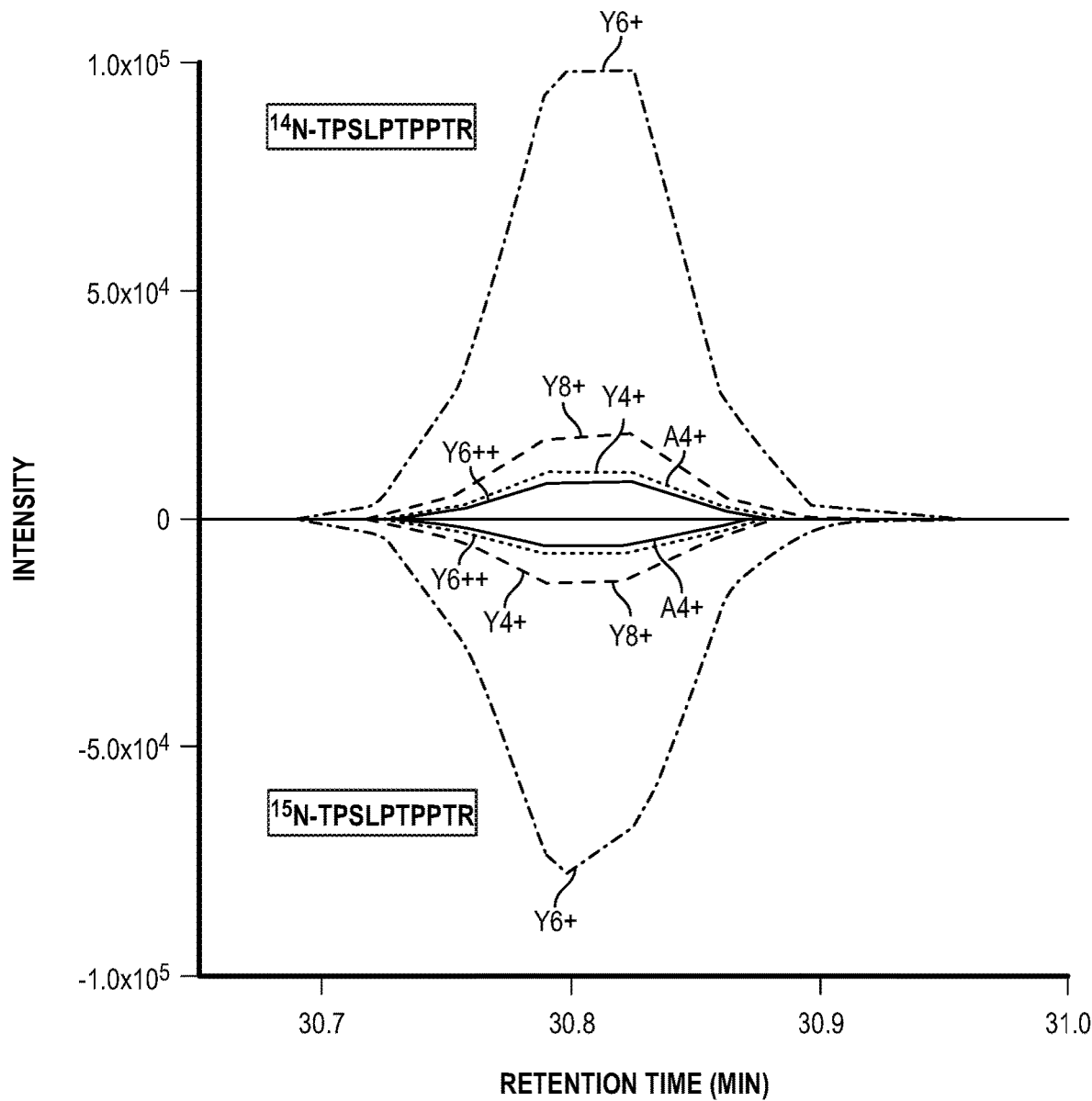
Figure 2:
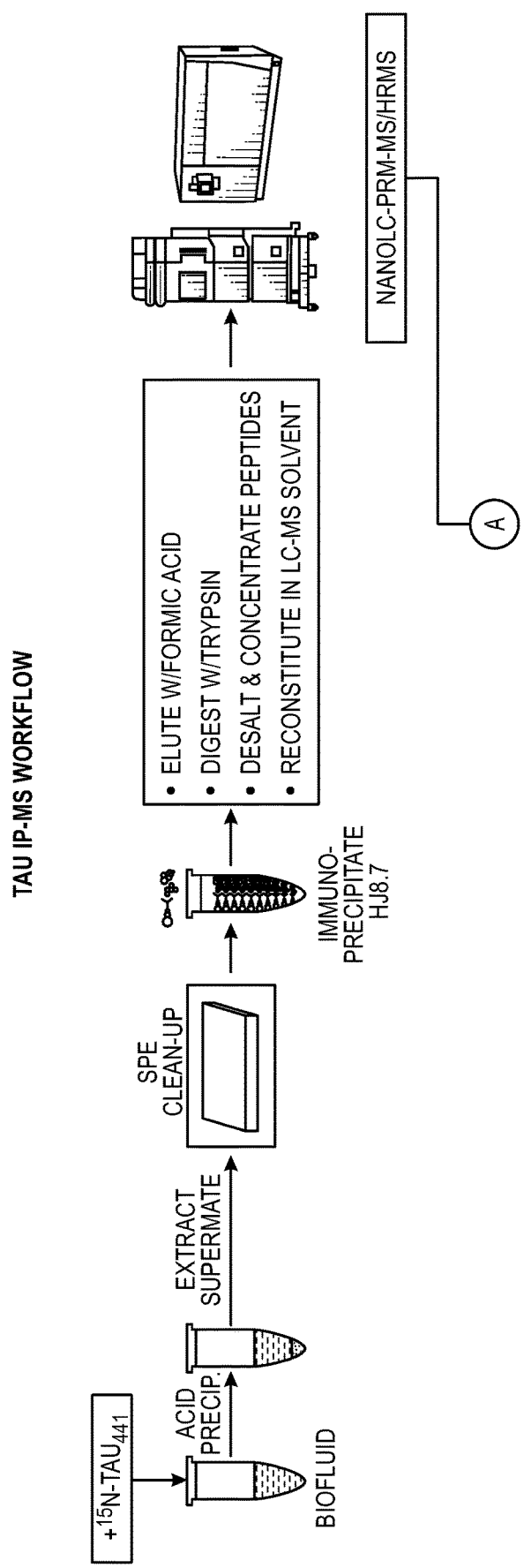
FIG. 2 shows the entire sample and standard preparation, processing, and analysis workflow.
Figure 2:
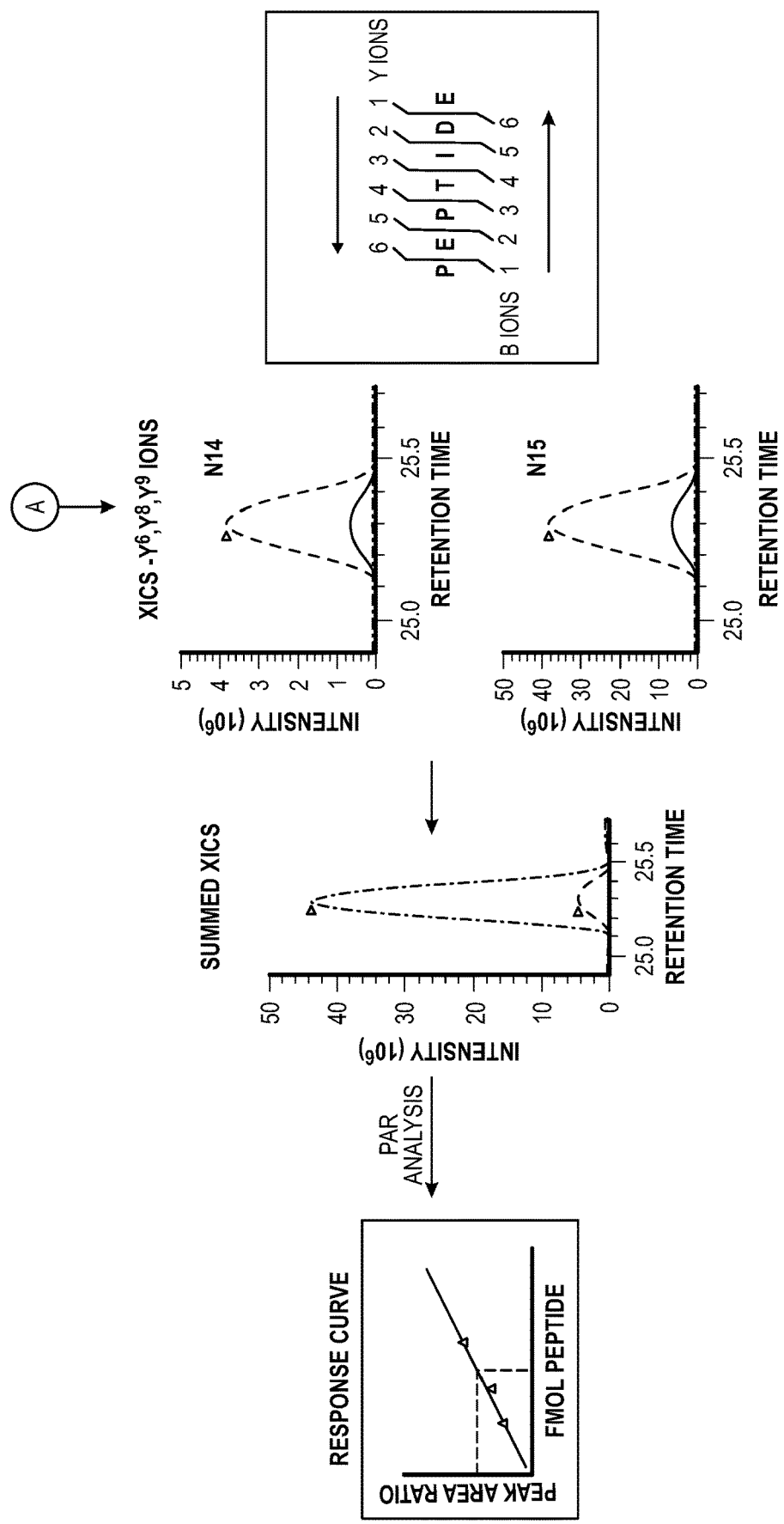

The present invention is based, in part, on the principle that stable isotope labeled proteins and peptides have a known, slightly greater molecular weight than their corresponding endogenous proteins and peptides, but they have identical physical or chemical properties, behave the same way in a mass spectrometer, except for their greater mass, which makes them ideal quantitative internal standards. Using the techniques provided herein, endogenous proteins, peptide fragments, and proteoforms are quantified and can be used to diagnose and/or treat a subject having or at risk of developing a neurological or neurodegenerative disorder. Accordingly, the present invention provides methods and kits useful for calculating the concentration of one or more proteins, peptide fragments, and proteoforms of interest in a subject.

The invention also provides a method to assess whether a therapeutic intervention affects the concentration of proteins, peptide fragments, and proteoforms in the subject, where the biomolecules are relevant to neurological or neurodegenerative diseases. Accordingly, the method may be used to determine the optimal doses and/or optimal dosing regimens of the therapeutic intervention. Additionally, the method may be used to determine which subjects respond better to a particular therapeutic intervention. For example, subjects with high protein, peptide fragment, proteoform concentrations may respond better to one therapeutic agent, whereas subjects with normal concentrations may be at lower risk for developing a neurodegenerative disorder and are not eligible to enroll in clinical trials of experimental therapeutic agents or interventions. Alternatively, subjects with one particular genotype or proteotype may respond better to a particular therapeutic agent than those with a different genotype or proteotype. Finally, by allowing isoform specific quantitation, the method may be used to determine whether a therapeutic agent can modulate the relative concentration of one isoform to another isoform of the same protein.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "subject" as used herein refers to any individual or patient to which the subject methods are performed. Generally, the subject is human, although as will be appreciated by those in the art, the subject may be an animal.

Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. In addition, the term "subject" may refer to a culture of cells, where the methods of the invention are performed in vitro to assess, for example, efficacy of a therapeutic agent.

As used herein, the terms "sample" and "biological sample" refer to any sample suitable for the methods provided by the present invention. A sample of cells used in the present method can be obtained from tissue samples or bodily fluid from a subject, or tissue obtained by a biopsy procedure (e.g., a needle biopsy) or a surgical procedure. In certain embodiments, the biological sample of the present invention is a sample of bodily fluid, e.g., cerebral spinal fluid (CSF), blood, plasma, urine, saliva, and tears.

As disclosed herein, stable isotope labeled Quantitation Internal Standards have a slightly higher molecular weight than their endogenous counterparts, but does not alter the physical or chemical properties of the proteins, peptide fragments, and proteoforms. Thus, these biomolecules and their stable isotope labeled counterparts will bind to antibodies and elute off a liquid chromatography column in an identical fashion. Sensitive instruments, such as mass spectrometers, provide the ability to measure small differences in mass between labeled and unlabeled biomolecules.

Accordingly, in one aspect, the invention provides a method of calculating the concentration of a biomolecule in a subject. In one embodiment, the method includes contacting a sample from the subject with a Quantitation Internal Standard. As used herein, a "Quantitation Internal Standard" refers to a known concentration of a stable isotope labeled biomolecule, which has a distinct molecular weight from other labeled or unlabeled biomolecules that may exist in the sample. Thereafter, a sensitive measuring device, such as a mass spectrometer, a tandem mass spectrometer, or a combination of both, is used to measure the ratio of labeled to unlabeled biomolecules. Since the physical properties of the labeled and unlabeled biomolecules are identical, the ratio measured by the mass spectrometer is identical to the ratio in the original sample. Thus, by adding a known amount of one or more biomolecules, each labeled with a unique isotopic label, the invention provides the ability to quantitate the amount of those biomolecules that have different isotopic composition.

As used herein, the term "biomolecule" refers to any organic molecule in a living organism. Exemplary biomolecules include, but are not limited to proteins, peptides, proteoforms. In one embodiment, the biomolecule is a peptide, such as a protein, that is synthesized in the central nervous system (CNS) of the subject. Exemplary proteins that can be measured by the methods of the invention include, but are not limited to, Tau and post-translationally modified such as phospho-Tau (associated with Alzheimer's Disease). In one embodiment, the protein whose in vivo concentration is measured may be Tau or its variants or isoforms. Exemplary isoforms of Tau whose concentrations may be measured include, but are not limited to, the following phosphorylated or unphosphorylated isoforms of Tau: Tau-4R2N, Tau-4R1N, Tau-4R0N, Tau-3R2N, Tau-3R1N, Tau-3R0N. The following shows a multiple sequence alignment of the 6 different isoforms of Tau.

| SEQ ID Nos. | | | | |
|---|---|---|---|---|
| 1 | 441 aa 4R/2N | MAEPRQEFEVMEDHAGTYGLGDRKDQGGYTMHQDQEGDTDAGLKESPLQTPTEDGSEEPG | 60 |
| 2 | 412 aa 4R/1N | MAEPRQEFEVMEDHAGTYGLGDRKDQGGYTMHQDQEGDTDAGLKESPLQTPTEDGSEEPG | 60 |
| 3 | 383 aa 4R/0N | MAEPRQEFEVMEDHAGTYGLGDRKDQGGYTMHQDQEGDTDAGLK | 44 |
| 4 | 410 aa 3R/2N | MAEPRQEFEVMEDHAGTYGLGDRKDQGGYTMHQDQEGDTDAGLKESPLQTPTEDGSEEPG | 60 |
| 5 | 381 aa 3R/1N | MAEPRQEFEVMEDHAGTYGLGDRKDQGGYTMHQDQEGDTDAGLKESPLQTPTEDGSEEPG | 60 |
| 6 | 352 aa 3R/0N | MAEPRQEFEVMEDHAGTYGLGDRKDQGGYTMHQDQEGDTDAGLK | 44 |
| | | ********************************************* | |
| 7 | 441 aa | SETSDAKSTPTAEDVTAPLVDEGAPGKQAAAQPHTEIPEGTTAEEAGIGDTPSLEDEAAG | 120 |
| 8 | 412 aa | SETSDAKSTPTAE---------------------------AEEAGIGDTPSLEDEAAG | 91 |
| 9 | 383 aa | -----------------------------------------AEEAGIGDTPSLEDEAAG | 62 |
| 10 | 410 aa | SETSDAKSTPTAEDVTAPLVDEGAPGKQAAAQPHTEIPEGTTAEEAGIGDTPSLEDEAAG | 120 |
| 11 | 381 aa | SETSDAKSTPTAE---------------------------AEEAGIGDTPSLEDEAAG | 91 |
| 12 | 352 aa | -----------------------------------------AEEAGIGDTPSLEDEAAG | 62 |
| | | ****************** | |
| 13 | 441 aa | HVTQARMVSKSKDGTGSDDKKAKGADGKTKIATPRGAAPPGQKGQANATRIPAKTPPAPK | 180 |
| 14 | 412 aa | HVTQARMVSKSKDGTGSDDKKAKGADGKTKIATPRGAAPPGQKGQANATRIPAKTPPAPK | 151 |
| 15 | 383 aa | HVTQARMVSKSKDGTGSDDKKAKGADGKTKIATPRGAAPPGQKGQANATRIPAKTPPAPK | 122 |
| 16 | 410 aa | HVTQARMVSKSKDGTGSDDKKAKGADGKTKIATPRGAAPPGQKGQANATRIPAKTPPAPK | 180 |
| 17 | 381 aa | HVTQARMVSKSKDGTGSDDKKAKGADGKTKIATPRGAAPPGQKGQANATRIPAKTPPAPK | 151 |
| 18 | 352 aa | HVTQARMVSKSKDGTGSDDKKAKGADGKTKIATPRGAAPPGQKGQANATRIPAKTPPAPK | 122 |
| | | ************************************************************ | |
| 19 | 441 aa | TPPSSGEPPKSGDRSGYSSPGSPGTPGSRSRTPSLPTPPTREPKKVAVVRTPPKSPSSAK | 240 |
| 20 | 412 aa | TPPSSGEPPKSGDRSGYSSPGSPGTPGSRSRTPSLPTPPTREPKKVAVVRTPPKSPSSAK | 211 |
| 21 | 383 aa | TPPSSGEPPKSGDRSGYSSPGSPGTPGSRSRTPSLPTPPTREPKKVAVVRTPPKSPSSAK | 182 |
| 22 | 410 aa | TPPSSGEPPKSGDRSGYSSPGSPGTPGSRSRTPSLPTPPTREPKKVAVVRTPPKSPSSAK | 240 |

-continued

| SEQ ID Nos. | | | |
|---|---|---|---|
| 23 | 381 aa | TPPSSGEPPKSGDRSGYSSPGSPGTPGSRSRTPSLPTPPTREPKKVAVVRTPPKSPSSAK | 211 |
| 24 | 352 aa | TPPSSGEPPKSGDRSGYSSPGSPGTPGSRSRTPSLPTPPTREPKKVAVVRTPPKSPSSAK | 182 |
| | | ************************************************************ | |
| 25 | 441 aa | SRLQTAPVPMPDLKNVKSKIGSTENLKHQPGGGKVQIINKKLDLSNVQSKCGSKDNIKHV | 300 |
| 26 | 412 aa | SRLQTAPVPMPDLKNVKSKIGSTENLKHQPGGGKVQIINKKLDLSNVQSKCGSKDNIKHV | 271 |
| 27 | 383 aa | SRLQTAPVPMPDLKNVKSKIGSTENLKHQPGGGKVQIINKKLDLSNVQSKCGSKDNIKHV | 242 |
| 28 | 410 aa | SRLQTAPVPMPDLKNVKSKIGSTENLKHQPGGGK | 274 |
| 29 | 381 aa | SRLQTAPVPMPDLKNVKSKIGSTENLKHQPGGGK | 245 |
| 30 | 352 aa | SRLQTAPVPMPDLKNVKSKIGSTENLKHQPGGGK | 216 |
| | | ********************************* | |
| 31 | 441 aa | PGGGSVQIVYKPVDLSKVTSKCGSLGNIHHKPGGGQVEVKSEKLDFKDRVQSKIGSLDNI | 360 |
| 32 | 412 aa | PGGGSVQIVYKPVDLSKVTSKCGSLGNIHHKPGGGQVEVKSEKLDFKDRVQSKIGSLDNI | 331 |
| 33 | 383 aa | PGGGSVQIVYKPVDLSKVTSKCGSLGNIHHKPGGGQVEVKSEKLDFKDRVQSKIGSLDNI | 302 |
| 34 | 410 aa | VQIVYKPVDLSKVTSKCGSLGNIHHKPGGGQVEVKSEKLDFKDRVQSKIGSLDNI | 329 |
| 35 | 381 aa | VQIVYKPVDLSKVTSKCGSLGNIHHKPGGGQVEVKSEKLDFKDRVQSKIGSLDNI | 300 |
| 36 | 352 aa | VQIVYKPVDLSKVTSKCGSLGNIHHKPGGGQVEVKSEKLDFKDRVQSKIGSLDNI | 271 |
| | | ****************************************************** | |
| 37 | 441 aa | THVPGGGNKKIETHKLTFRENAKAKTDHGAEIVYKSPVVSGDTSPRHLSNVSSTGSIDMV | 420 |
| 38 | 412 aa | THVPGGGNKKIETHKLTFRENAKAKTDHGAEIVYKSPVVSGDTSPRHLSNVSSTGSIDMV | 391 |
| 39 | 383 aa | THVPGGGNKKIETHKLTFRENAKAKTDHGAEIVYKSPVVSGDTSPRHLSNVSSTGSIDMV | 362 |
| 40 | 410 aa | THVPGGGNKKIETHKLTFRENAKAKTDHGAEIVYKSPVVSGDTSPRHLSNVSSTGSIDMV | 389 |
| 41 | 381 aa | THVPGGGNKKIETHKLTFRENAKAKTDHGAEIVYKSPVVSGDTSPRHLSNVSSTGSIDMV | 360 |
| 42 | 352 aa | THVPGGGNKKIETHKLTFRENAKAKTDHGAEIVYKSPVVSGDTSPRHLSNVSSTGSIDMV | 331 |
| | | *********************************************************** | |
| 43 | 441 aa | DSPQLATLADEVSASLAKQGL | 441 |
| 44 | 412 aa | DSPQLATLADEVSASLAKQGL | 412 |
| 45 | 383 aa | DSPQLATLADEVSASLAKQGL | 383 |
| 46 | 410 aa | DSPQLATLADEVSASLAKQGL | 410 |
| 47 | 381 aa | DSPQLATLADEVSASLAKQGL | 381 |
| 48 | 352 aa | DSPQLATLADEVSASLAKQGL | 352 |
| | | ********************* | |

By way of example and not limitation, it is noted that several unique isoforms of Tau exist in CSF and plasma, and that these isoforms can be post-translationally modified in several ways including phosphorylation. Trypsin digestion of Tau yields several peptides which may or may not be unique to each isoform, see Table 1. Thus, quantitation of some of these peptides allows for calculation of the concentration of these isoforms in the original biological fluid.

TABLE 1

| SEQ ID NO. | Peptide Sequence | Includes Tau 441 Residues With Cleavage Residues | Isoforms | CSF (ng/mL) | CSF Curve $R^2$ | Plasma LLOQ (ng/mL) | Plasma Std Curve $R^2$ |
|---|---|---|---|---|---|---|---|
| 49 | R.QEFEVMEDHAGTYGLGDR.K | 6-23 | Total | 0.08 | 0.9987 | nd | — |
| 50 | R.KDQGGYTMHQDQEGDTDAGLK.E | 24-44 | Total | 0.08 | 0.9999 | nd | — |
| 51 | K.ESPLQTPTEDGSEEPGSETSDAK.S | 45-67 | 1N/2N | 0.03 | 0.9932 | 0.05 | 0.9932 |
| 52 | K.STPTAEDVTAPLVDEGAPGK.Q | 68-87 | 2N | 0.03 | 0.9956 | 0.05 | 0.9956 |
| 53 | K.QAAAQPHTEIPEGTTAEEAGIGDTPSLEDEAAGHVTQAR.M | 88-126 | 2N | 0.03 | 0.9929 | 0.05 | 0.9397 |
| 54 | K.IATPR.G | 151-155 | Total | 0.03 | 0.9979 | 2.5 | 0.8603 |
| 55 | R.GAAPPGQK.G | 156-163 | Total | nd | — | 2.5 | 0.9937 |
| 56 | K.TPPAPK.T | 175-180 | Total | 0.25 | 0.9982 | nd | — |
| 57 | K.TPPSSGEPPK.S | 181-190 | Total | 0.03 | 0.9948 | nd | — |
| 58 | R.SGYSSPGSPGTPGSR.S | 195-209 | Total | 0.003 | 0.9974 | 0.05 | 0.9937 |
| 59 | R.TPSLPTPPTR.E | 212-221 | Total | 0.003 | 0.9994 | 0.05 | 0.9994 |
| 60 | R.TPSLPTPPTREPK.K | 212-224 | Total | 0.5 | 0.9988 | 2.5 | 0.9941 |

TABLE 1-continued

| SEQ ID NO. | Peptide Sequence | Includes Tau 441 Residues With Cleavage Residues | Isoforms | CSF (ng/mL) | CSF Curve $R^2$ | Plasma LLOQ (ng/mL) | Plasma Std Curve $R^2$ |
|---|---|---|---|---|---|---|---|
| 61 | K.IGSTENLK.H | 260-267 | Total | 0.03 | 0.9886 | 0.05 | 0.9988 |
| 62 | K.VQIINK.K | 275-280 | 4R | 0.01 | 0.9831 | 0.5 | 0.9967 |
| 63 | K.VQIVYKPVDLSK.V | 275-286 | 3R | 10 | nd | 10 | nd |
| 64 | K.LDLSNVQSK.C | 282-290 | 4R | 0.05 | 0.9910 | 0.05 | 0.9969 |
| 65 | K.HVPGGGSVQIVYKPVDLSK.V | 299-317 | 4R | 0.05 | 0.9999 | 0.05 | 0.9883 |
| 66 | K.IGSLDNITHVPGGGNK.K | 354-369 | Total | 0.05 | 0.999 | 0.05 | 0.9977 |
| 67 | K.TDHGAEIVYK.S | 386-395 | Total | 0.1 | 0.9985 | 0.05 | 0.9710 |
| 68 | K.SPVVSGDTSPR.H | 396-406 | Total | 0.05 | 0.9952 | 0.5 | 0.9819 |

As such, the methods provide the ability to measure concentrations of various isoforms of Tau, such as fragments produced after digestion with an endoprotease (e.g., trypsin, LysN, or V8 protease). Exemplary fragments of Tau isoforms include but are not limited to regions of Tau that are different between the different isoforms and their boundaries, such as the N-terminal region (2N/1N/0N) and the C-terminal repeat region (4R/3R).

As used herein, the term "nucleic acid" refers to DNA, RNA, single-stranded, double-stranded or triple stranded and any chemical modifications thereof. Virtually any modification of the nucleic acid is contemplated. A "nucleic acid molecule" can be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule.

The terms "polypeptide," "peptide" and "protein" are used interchangeably herein to refer to two or more amino acid residues joined to each other by peptide bonds or modified peptide bonds, i.e., peptide isosteres. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer. "Polypeptide" refers to both short chains, commonly referred to as peptides, oligopeptides or oligomers, and to longer chains, generally referred to as proteins. Polypeptides may contain amino acids other than the 20 gene-encoded amino acids. Likewise, "protein" refers to at least two covalently attached amino acids, which includes proteins, polypeptides, oligopeptides and peptides. A protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration.

Several different moieties may be used to label the biomolecule of interest. Generally speaking, the two types of labeling moieties utilized in the method of the invention are radioactive isotopes and non-radioactive (stable) isotopes. In one embodiment, non-radioactive isotopes may be used and measured by mass spectrometry. Preferred stable isotopes include deuterium ($^2$H), $^{13}$C, $^{15}$N, $^{17\ or\ 18}$O, and $^{33,\ 34,\ or\ 36}$S, but it is recognized that a number of other stable isotopes that change the mass of an atom by more or less neutrons than is seen in the prevalent native form would also be effective. A suitable label generally will change the mass of the biomolecule under study such that it can be detected in a mass spectrometer. In one embodiment, the biomolecule to be measured may be a peptide or protein, and the labeled moiety may be an amino acid comprising a non-radioactive isotope (e.g., $^{13}$C). In another embodiment, the biomolecule to be measured may be a nucleic acid, and the labeled moiety may be a nucleoside triphosphate comprising a non-radioactive isotope (e.g., $^{15}$N). Alternatively, a radioactive isotope may be used, and the labeled biomolecules may be measured with a scintillation counter (or via nuclear scintigraphy) as well as by a mass spectrometer. One or more labeled moieties may be used simultaneously or in sequence.

Thus, in one embodiment, when the method is employed to measure the concentration of proteins, the labeled moiety typically will be an amino acid. Those of skill in the art will appreciate that several amino acids may be used to provide the label of biomolecules. Generally, the choice of amino acid is based on a variety of factors such as: (1) The amino acid generally is present in at least one residue of the protein or peptide of interest. (2) The amino acid is generally able to reach the site of protein production and rapidly equilibrate tissue or cellular barriers. And (3) commercial availability of the desired amino acid (i.e., some amino acids are much more expensive or harder to manufacture than others).

In one embodiment, the amino acid is an essential amino acid (not produced by the body), so that a higher percent of labeling may be achieved. In another embodiment, the amino acid is a non-essential amino acid. Exemplary amino acids include, but are not limited to, leucine, isoleucine, and phenylalanine. As such, in one embodiment, the labeled amino acid is one or more of a $^{15}$N-labeled amino acid, a $^{13}C_x$-labeled phenylalanine, where x=1 to 9, a $^{13}C_x$-labeled isoleucine, where x=1 to 6. For example, $^{13}C_6$-phenylalanine, which contains six $^{13}C$ atoms, may be used to label a biomolecule of interest (e.g., a CNS derived protein). In another embodiment, $^{13}C_6$-leucine may be used to label a biomolecule of interest (e.g., a CNS derived protein). In yet another embodiment, $^{13}C_6$-leucine is used to label amyloid-beta (Aβ).

There are numerous commercial sources of labeled amino acids, both non-radioactive isotopes and radioactive isotopes. Generally, the labeled amino acids may be produced either biologically or synthetically. Biologically produced amino acids may be obtained from an organism (e.g., kelp/seaweed) grown in an enriched mixture of $^{13}C$, $^{15}N$, or another isotope that is incorporated into amino acids as the organism produces proteins. The amino acids are then separated and purified. Alternatively, amino acids may be made with known synthetic chemical processes.

Once disease is established and a treatment protocol is initiated, the methods of the invention may be repeated on a regular basis to monitor the concentration(s) of biomolecule(s) of interest in the subject. The results obtained from successive assays may be used to show the efficacy of treatment over a period ranging from several days to months. Accordingly, another aspect of the invention is directed to methods for monitoring a therapeutic regimen for treating a subject having a neurological or neurodegenerative disorder. A comparison of the concentration(s) of biomolecule(s) of interest prior to and during therapy will be indicative of the efficacy of the therapy. Therefore, one skilled in the art will be able to recognize and adjust the therapeutic approach as needed.

The method of the invention provides that a sample be obtained from the subject such that the in vivo concentration of one or more biomolecules of interest can be determined. In one embodiment, the sample is a body fluid. Suitable body fluids include, but are not limited to, cerebral spinal fluid (CSF), blood plasma, blood serum, urine, saliva, perspiration, and tears. It should be understood that biological fluids typically contain a multitude of quantifiable biomolecules. For example, where the sample is CSF, exemplary biomolecules that can be quantified include, but are not limited to, Tau, variants of Tau, amyloid-beta protein, variants of amyloid-beta protein (Aβ), digestion products of amyloid-beta protein, amyloid precursor protein (APP), apolipoprotein E, apolipoprotein J, alpha-synuclein, or any combination thereof. In another embodiment, the sample is a tissue sample, such as a sample of tissue from the central nervous system (CNS). The sample generally will be collected using standard procedures well known to those of skill in the art.

In one embodiment, the sample is a CNS sample, which includes, but is not limited to, tissue from the central nervous system, which comprises brain tissue and spinal cord tissue. In one embodiment of the invention, the CNS sample may be taken from brain tissue, including, but not limited to, tissue from the forebrain (e.g., cerebral cortex, basal ganglia, hippocampus), the interbrain (e.g., thalamus, hypothalamus, subthalamus), the midbrain (e.g., tectum, tegmentum), or the hindbrain (e.g., pons, cerebellum, medulla oblongata). In another embodiment, the CNS sample may be collected from spinal cord tissue. In still other embodiments, CNS samples from more than one CNS region may be taken. Accordingly, the concentration of a biomolecule of interest may be measured in different CNS samples, e.g., in the cortex and the hippocampus, simultaneously.

CNS samples may be obtained by known techniques. For instance, brain tissue or spinal cord tissue may be obtained via dissection or resection. Alternatively, CNS samples may be obtained using laser microdissection. The subject may or may not have to be sacrificed to obtain the sample, depending on the CNS sample desired and the subject utilized.

In general, when the biomolecule under study is a peptide or protein, the invention provides that a first sample may be taken from a subject prior to administration of the therapeutic agent to provide a baseline concentration. After administration of the therapeutic agent, one or more samples are obtained from the subject. As will be appreciated by those of skill in the art, the number of samples and when the samples are taken generally will depend upon a number of factors such as: the type of analysis, type of administration, the protein of interest, the rate of metabolism, the type of detection, and the type of subject.

It should be understood that if samples at different time-points are desired, more than one subject may be used. For instance, one subject may be used for a baseline sample, another subject for a time-point of one-hour post administration of the therapeutic agent, another subject for a time-point six hours post administration of the therapeutic agent.

Accordingly, the present invention provides that detection of the amount of labeled biomolecule and the amount of unlabeled biomolecule in the sample may be used to determine the ratio of labeled biomolecule to unlabeled biomolecule, which in turn, may be used to calculate the concentration of the biomolecule of interest in the subject. In one embodiment, the ratio is determined by means of detecting changes in mass of the labeled biomolecule (e.g., peptide or protein) with respect to the unlabeled biomolecule. Exemplary means for detecting differences in mass between the labeled and unlabeled biomolecules include, but are not limited to, liquid chromatography mass spectrometry, gas chromatography mass spectrometry, MALDI-TOF mass spectrometry, and tandem mass spectrometry.

However, prior to detecting the ratio of labeled biomolecule to unlabeled biomolecule, it may be desirable to isolate and/or separate the biomolecule of interest from other biomolecules in the sample. Thus, in one embodiment, immunoprecipitation may be used to isolate and purify the biomolecule (e.g., peptide or protein) of interest before it is analyzed. In another embodiment, the biomolecule of interest may be isolated or purified by affinity chromatography or immunoaffinity chromatography. Alternatively, mass spectrometers having chromatography setups may be used to separate biomolecules without immunoprecipitation, and then the biomolecule of interest may be measured directly. In an exemplary embodiment, the protein of interest may be immunoprecipitated and then analyzed by a liquid chromatography system interfaced with a tandem MS unit equipped with an electrospray ionization source (LC-ESI-tandem MS). One example of using 3 different antibodies to immunoprecipitate Tau protein from 3 aliquots of the same human CSF sample, followed by digestion of Tau protein, and quantitation of the relative abundance of different Tau peptides is shown in Table 2. This aspect includes the observation that different antibodies have different affinity for different portions of the Tau protein, and the selection of immunoprecipitation antibody can be used to focus the quantitative analysis on different portions or proteoforms of the Tau biomolecule.

TABLE 2

| SEQ ID Nos. | Peptide Sequence (Residue) | HJ8.5 | HJ8.7 | Tau12 |
|---|---|---|---|---|
| 69 | QEFEVMEDHAGTYHLHDR (6-23) | 0.97 | 0.68 | 1.00 |
| 70 | KDQGGYTMHQDQEGDTDAGLK (24-44) | 1.00 | 0.84 | 0.15 |
| 71 | ESPLQTPTEDFSEEPGSETSDAK (45-67) | 0.74 | 1.00 | 0.92 |
| 72 | STPTAEDVTAPLVDEGAPGK (68-87) | 0.47 | 1.00 | 0.47 |
| 73 | QAAAQPHTEIPEGTTAEEAGIGDTPSL EDEAAGHVTQAR (88-126) | 0.36 | 1.00 | 0.59 |
| 74 | IATPR (151-155) | 0.55 | 1.00 | 0.87 |
| 75 | TPPAPK (175-180) | 0.97 | 1.00 | 0.99 |
| 76 | TPPSSGEPPK (181-190) | 0.52 | 1.00 | 0.46 |
| 77 | SGYSSPGSPGTPGSR (195-209) | 0.83 | 0.80 | 1.00 |
| 78 | TPSLPTPPTR (212-221) | 0.49 | 0.86 | 1.00 |
| 79 | TPSLPTPPTREPK (212-224) | 0.94 | 0.94 | 1.00 |
| 80 | IGSTENLK (260-267) | 0.37 | 1.00 | 0.86 |
| 81 | VQIINK (275-280) | 0.36 | 1.00 | 0.31 |
| 82 | LDLSNVWSK (282-290) | 0.08 | 0.04 | 1.00 |
| 83 | HVPGGGSVQICYKPVDLSK (299-316) | 0.40 | 1.00 | 0.82 |
| 84 | IGSLDNITHVPGGGNK (354-369) | 0.61 | 1.00 | 0.86 |
| 85 | TDHGAEIVYK (386-395) | 0.44 | 1.00 | 0.68 |
| 86 | SPVVSGDTSPR (396-406) | 1.00 | 0.39 | 0.42 |

Peptide Intensity
*Values are reported as a fraction of the abundance for the immuno-precipitation antibody that provided the highest abundance (1.0) for that specific Tau peptide In another aspect, the invention provides that multiple biomolecules in the same sample may be measured simultaneously. That is, both the amount of unlabeled and labeled biomolecule may be detected and measured separately or at the same time for multiple biomolecules. As such, the invention provides a useful method for screening changes in concentration, of one or more biomolecules on a large scale (i.e., proteomics/metabolomics) and provides a sensitive means to detect and measure biomolecules involved in the underlying pathophysiology. In this aspect, the invention also provides a means to measure multiple types of biomolecules. In this context, for example, a protein and a lipid may be measured simultaneously or sequentially.

Once the amount of labeled and unlabeled biomolecule has been detected in a sample, the ratio or percent of labeled biomolecule to unlabeled biomolecule may be determined. Thereafter, the concentration of the unlabeled biomolecule in the sample can be determined. In other words, since a known amount of labeled biomolecule is added to an unknown amount of biomolecules and the ratio of labeled to unlabeled is measured, the concentration of the unlabeled biomolecules can be calculated from the ratio as follows:

Concentration of unlabeled=(ratio of unlabeled to labeled)×(concentration of labeled). (i)

The equation may be simplified as:

Concentration of unlabeled=(ratio of unlabeled: Quantitation Internal Standard)×(concentration of Quantitation Internal Standard). (ii)

Conversely, if a known amount of unlabeled is added to an unknown amount labeled the concentration of the labeled can be calculated as follows:

Concentration of labeled=(ratio of labeled to unlabeled)×(concentration of unlabeled). (iii)

In addition, if a known amount of biomolecule 1, labeled with label 1, is added to an unknown amount of biomolecule 2, labeled with label 2, the concentration of the biomolecule 2 can be calculated as follows:

Concentration of label 2=(ratio of label 2 to label 1)×(concentration of label 1). (iv)

Similarly, if a known amount of biomolecule 1, labeled with label 1, is added to an unknown amount of biomolecule 2, labeled with label 2, and biomolecule 3, labeled with label 3, the concentration of the biomolecule 2 and biomolecule 3 can be calculated as follows:

Concentration of label 2=(ratio of label 2 to label 1)×(concentration of label 1) (v)

Concentration of label 3=(ratio of label 3 to label 1)×(concentration of label 1). (vi)

Finally, if a known amount of biomolecule 1, labeled with label 1, is added to an unknown amount of biomolecule 2, labeled with label 2, and an unknown amount of unlabeled biomolecule 3, the concentration of the biomolecule 2 and unlabeled biomolecule can be calculated as follows:

Concentration of label 2=(ratio of label 2 to label 1)×(concentration of label 1) (vii)

Concentration of unlabeled=(ratio of unlabeled to label 1)×(concentration of label 1). (viii)

In another embodiment, the methods further include the step of normalizing the calculated concentration to a standard curve based on the curve fitting equation generated by the standard curve. The standard curve used herein is generated by determining two or more ratios of unlabeled biomolecules to their respective Quantitation Internal Standards, where the concentration of the unlabeled biomolecule of interest is known.

In another aspect, the invention allows measurement of the labeled and unlabeled protein at the same time, so that the ratio of labeled to unlabeled protein, as well as other calculations, may be made.

In one aspect, Tau is isolated from the biologic samples by immunoprecipitation using an antibody that recognizes Tau. In this embodiment, the isolated peptides are eluted from the antibody, for example by using formic acid and then digested with trypsin or another protease. This invention measures the concentration of Tau peptides.

The term "antibody" as used in this invention is meant to include intact molecules of polyclonal or monoclonal antibodies, as well as fragments thereof, such as Fab and $F(ab')_2$, Fv and SCA fragments which are capable of binding an epitopic determinant. The term "specifically binds" or "specifically interacts," when used in reference to an antibody means that an interaction of the antibody and a particular epitope has a dissociation constant of at least about $1\times10^{-6}$, generally at least about $1\times10^{-7}$, usually at least about $1\times10^{-8}$, and particularly at least about $1\times10^{-9}$ or $1\times10^{-10}$ or less.

The method of the invention may be used to diagnose or monitor the progression of a neurological or neurodegenerative disease by measuring the in vivo concentration of one or more biomolecules of interest in a subject. Additionally, the methods of the invention may be used to monitor the treatment of a neurological or neurodegenerative disease by measuring the in vivo concentration of a biomolecule of interest in a subject. The concentration of the biomolecule may be linked to a neurological or neurodegenerative disease such that any increase or decrease may be indicative of the presence or progression of the disease. Thus, the calculated concentration of one or more biomolecules of interest may be compared to the concentration of the same biomolecules in a corresponding normal sample, to the concentration of the same biomolecules in a subject of known neurological or neurodegenerative disease state, to the concentration of the same biomolecules from the same subject determined at an earlier time, or any combination thereof.

In addition, such methods may help identify an individual as having a predisposition for the development of the disease or may provide a means for detecting the disease prior to the appearance of actual clinical symptoms. A more definitive diagnosis of this type may allow health professionals to employ preventative measures or aggressive treatment earlier thereby preventing the development or further progression of the disease.

As used herein a "corresponding normal sample" refers to a sample from the same organ and/or of the same type as the sample being examined In one aspect, the corresponding normal sample comprises a sample of cells obtained from a healthy individual. Such a corresponding normal sample can, but need not be, from an individual that is age-matched and/or of the same sex as the individual providing the sample being examined In another aspect, the corresponding normal sample comprises a sample of cells obtained from an otherwise healthy portion of tissue of the subject from which the sample being tested is obtained.

Reference to the concentration of biomolecules in a subject of known neurological or neurodegenerative disease state includes a predetermined concentration of a biomolecule linked to a neurological or neurodegenerative disease. Thus, the concentration may be compared to a known concentration of biomolecules obtained from a sample of a single individual or may be from an established cell line of the same type as that of the subject. In one aspect, the established cell line can be one of a panel of such cell lines, wherein the panel can include different cell lines of the same type of disease and/or different cell lines of different diseases associated with the same biomolecule. Such a panel of cell lines can be useful, for example, to practice the present method when only a small number of cells can be obtained from the subject to be treated, thus providing a surrogate sample of the subject's cells, and also can be useful to include as control samples in practicing the present methods.

Exemplary neurological or neurodegenerative diseases that may be linked to the concentration ranges of biomolecules of interest include, but are not limited to, Alzheimer's Disease, Pick's Disease, Parkinson's Disease, stroke, frontal temporal dementias (FTDs), Huntington's Disease, progressive supranuclear palsy (PSP), corticobasal degeneration (CBD), aging-related disorders and dementias, Multiple Sclerosis, Prion Diseases (e.g., Creutzfeldt-Jakob Disease, bovine spongiform encephalopathy or Mad Cow Disease, and scrapie), Lewy Body Disease, schizophrenia, Amyotrophic Lateral Sclerosis (ALS or Lou Gehrig's Disease) or other motor neuron diseases, restless legs syndrome, epilepsy or other seizure disorders, tremors, depression, mania, anxiety disorders, brain trauma or injury, narcolepsy, insomnia or other sleep disorders, autism, normal pressure hydrocephalus, pain disorders or syndromes, migraines, cluster headaches or other forms of headache, spinocerebellar disorders, muscular dystrophies, myasthenia gravis, retinitis pigmentosa or other forms of retinal degeneration. It is also envisioned that the method of the invention may be used to study the normal physiology, metabolism, and function of the CNS.

In another aspect, the present invention provides a method for assessing whether a therapeutic agent used to treat a neurological or neurodegenerative disease affects the concentration of a biomolecule of interest in the subject. For example, the concentration of the biomolecule may be measured to determine if a given therapeutic agent results in an increase, or a decrease in the concentration of the biomolecule. In one embodiment, the method is performed in vivo, as herein described. In another embodiment, the method is performed in vitro utilizing a culture of cells, where the culture of cells is the "subject" in the methods described herein. Accordingly, use of the methods provided herein will allow those of skill in the art to accurately determine the degree of change in the concentration of the biomolecule of interest, and correlate these measurements with the clinical outcome of the disease modifying treatment. Results from this aspect of the invention, therefore, may help determine the optimal doses and frequency of doses of a therapeutic agent, may assist in the decision-making regarding the design of clinical trials, and may ultimately accelerate validation of effective therapeutic agents for the treatment of neurological or neurodegenerative diseases.

Thus, the method of the invention may be used to predict which subjects will respond to a particular therapeutic agent. For example, subjects with increased concentrations of a particular biomolecule may respond to a particular therapeutic agent differently than subjects with decreased concentrations of the biomolecule. In particular, results from the method may be used to select the appropriate treatment (e.g., an agent that blocks the production of the biomolecule or an agent that increases the clearance of the biomolecule) for a particular subject. Similarly, results from the method may be used to select the appropriate treatment for a subject having a particular genotype.

Those of skill in the art will appreciate that the therapeutic agent can and will vary depending upon the neurological or neurodegenerative disease or disorder to be treated and/or the biomolecule whose metabolism is being analyzed. In embodiments in which the biomolecule is Tau, non-limiting examples of suitable therapeutic agents include Tau metabolism modulators, Tau kinase inhibitors, cathepsin D inhibitors, Tau autophagy activators, and Tau aggregation inhibitors. Other suitable AD therapeutic agents include hormones, neuroprotective agents, and cell death inhibitors. Many of the above mentioned therapeutic agents may also affect the in vivo metabolism of other proteins implicated in neurodegenerative disorders. Furthermore, therapeutic agents that may affect the in vivo metabolism of synuclein include sirtuin 2 inhibitors, synuclein aggregation inhibitors, proteasome inhibitors, etc.

The therapeutic agent may be administered to the subject in accordance with known methods. Typically, the therapeutic agent will be administered orally, but other routes of administration such as parenteral or topical may also be used. The amount of therapeutic agent that is administered to the subject can and will vary depending upon the type of agent, the subject, and the particular mode of administration. Those skilled in the art will appreciate that dosages may be determined with guidance from Goodman & Goldman's The Pharmacological Basis of Therapeutics, Tenth Edition (2001), Appendix II, pp. 475-493, and the Physicians' Desk Reference.

It should be understood that the methods of the invention described herein can be adapted to a high throughput format, thus allowing the examination of a plurality (i.e., 2, 3, 4, or more) of samples and/or biomolecules, which independently can be the same or different, in parallel. A high throughput format provides numerous advantages. For example, a high throughput format allows for the examination/quantitation of two, three, four, etc., different biomolecules, alone or in combination, of a subject. Finally, a high throughput format allows, for example, control samples (positive controls and or negative controls) to be run in parallel with test samples. In addition, a high throughput method may allow immunoprecipitation of multiple proteins at the same time using multiple antibodies.

In another aspect, the invention provides a kit for performing the methods of the invention. In one embodiment, a kit is provided for diagnosing and/or monitoring the progression or treatment of a neurological or neurodegenerative disease in a subject. The kit may further include an appropriate Quantitation Internal Standard and means for obtaining a biological sample at regular time intervals from the subject. In certain embodiments, the kit will also include instructions for detecting and determining the ratio of labeled to unlabeled biomolecules of interest over time and for calculating the concentration of the endogenous unlabeled biomolecule. In one embodiment, the instructions will disclose methods for comparing the calculated concentration to certain standards and/or controls as disclosed herein.

In another embodiment, the kit of the invention provides a compartmentalized carrier including one or more containers containing the Quantitation Internal Standard and the various means for performing the methods of the invention.

The following examples are provided to further illustrate the advantages and features of the present invention but are not intended to limit the scope of the invention. While they are typical of those that might be used, other procedures, methodologies, or techniques known to those skilled in the art may alternatively be used.

EXAMPLE

Quantitation of Tau by SISAQ $^{15}$N labeled Tau was used as Quantitation Internal Standard and spiked into a standard curve of samples containing concentrations of Tau ranging from 0.05 pg/mL to 100 pg/mL. In addition, the Quantitation Internal Standard was spiked into CSF and plasma from two different individuals. Tau was isolated from the samples using immunoprecipitation and then digested with trypsin and analyzed by mass spectrometry. The ratio of unlabeled endogenous Tau to Quantitation Internal Standard was calculated for all samples and a standard curve generated. The standard curve was linear in the range tested (0.05 pg/mL to 100 pg/mL) and was used to calculate the concentration of Tau in the CSF and plasma samples. The concentration of Tau was approximately 5 pg/mL in the CSF samples and around 0.1 pg/mL in plasma, and the intra- and inter-assay CV for triplicate measures of CSF and plasma Tau concentrations was less than 25%. Our data show that regardless of the concentration, Tau can be reliably and reproducibly measured using the invention methods. Examples of the intra-assay and inter-assay reliability (% CV) for quantifying several Tau peptides present in human CSF are shown in Tables 3 & 4. The intra-assay reliability (Table 3) was calculated by triplicate analysis of a single pooled human CSF sample where these injection replicate analyses were dispersed among many other standard curve samples and unknown samples included in the same analytical run. The inter-assay reliability (Table 4) was calculated by triplicate analysis of a single human CSF pool that was prepared and analyzed on 3 separate days (process replicates) in different analytical runs that included many other samples and standards.

TABLE 3

| SEQ. ID. Nos. | Inter-Assay Analysis Peptide Sequence (Residue #s) | Calculated Concentration (ng/mL) | | | Average Concentration (ng/mL) | Standard Deviation | % CV |
|---|---|---|---|---|---|---|---|
| | | Replicate 1 | Replicate 2 | Replicate 3 | | | |
| 87 | QEFEVMEDHAGTYHLHDR (6-23) | 3.174 | 3.220 | 3.111 | 3.168 | 0.055 | 1.7 |
| 88 | KDQGGYTMHQDQEGDTDAGLK (24-44) | 3.516 | 3.653 | 3.845 | 3.672 | 0.165 | 4.5 |
| 89 | ESPLQTPTEDFSEEPGSETSDAK (45-67) | 1.738 | 1.885 | 1.852 | 1.825 | 0.078 | 4.2 |
| 90 | STPTAEDVTAPLVDEGAPGK (68-87) | 0.223 | 0.212 | 0.215 | 0.216 | 0.006 | 2.6 |
| 91 | QAAAQPHTEIPEGTTAEEAGIGDTPSLE DEAAGHVTQAR (88-126) | 0.174 | 0.158 | 0.199 | 0.177 | 0.020 | 11.5 |
| 92 | IATPR (151-155) | 2.074 | 2.190 | 1.315 | 1.860 | 0.475 | 25.6 |
| 93 | TPPAPK (175-180) | 1.317 | 1.499 | 1.598 | 1.471 | 0.142 | 9.7 |
| 94 | TPPSSGEPPK (181-190) | 1.418 | 1.551 | 1.733 | 1.567 | 0.158 | 10.1 |
| 95 | SGYSSPGSPGTPGSR (195-209) | 1.240 | 1.289 | 1.047 | 1.192 | 0.128 | 10.7 |
| 96 | TPSLPTPPTR (212-221) | 1.191 | 1.259 | 1.230 | 1.227 | 0.034 | 2.8 |

TABLE 3-continued

| SEQ. ID. Nos. | Inter-Assay Analysis Peptide Sequence (Residue #s) | Calculated Concentration (ng/mL) | | | Average Concentration (ng/mL) | Standard Deviation | % CV |
|---|---|---|---|---|---|---|---|
| | | Day 1 | Day 2 | Day 3 | | | |
| 97 | QEFEVMEDHAGTYHLHDR (6-23) | 2.935 | 3.898 | 3.174 | 3.336 | 0.501 | 15.0 |
| 98 | KDQGGYTMHQDQEGDTDAGLK (24-44) | 2.419 | 2.870 | 3.516 | 2.935 | 0.552 | 18.8 |
| 99 | ESPLQTPTEDFSEEPGSETSDAK (45-67) | 1.488 | 2.003 | 1.738 | 1.743 | 0.258 | 14.8 |
| 100 | STPTAEDVTAPLVDEGAPGK (68-87) | 0.217 | 0.274 | 0.223 | 0.238 | 0.031 | 13.2 |
| 101 | QAAAQPHTEIPEGTTAEEAGIGDTPSLEDEAAGHVTQAR (88-126) | 0.184 | 0.218 | 0.174 | 0.192 | 0.023 | 12.2 |
| 102 | IATPR (151-155) | 1.302 | 1.587 | 2.074 | 1.654 | 0.390 | 23.6 |
| 103 | TPPAPK (175-180) | 1.423 | 1.310 | 1.317 | 1.350 | 0.063 | 4.7 |
| 104 | TPPSSGEPPK (181-190) | 1.177 | 1.686 | 1.418 | 1.427 | 0.255 | 17.9 |
| 105 | SGYSSPGSPGTPGSR (195-209) | 1.195 | 1.435 | 1.240 | 1.290 | 0.128 | 9.9 |
| 106 | TPSLPTPPTR (212-221) | 1.004 | 1.129 | 1.191 | 1.108 | 0.095 | 8.6 |

This illustrates the feasibility of using stable isotope labeled Tau as a quantitation internal standard and relating the ratio of unlabeled to labeled Tau to a standard curve to allow for measurement of concentrations of Tau in unknown samples.

Although the invention has been described with reference to the above example, it will be understood that modifications and variations are encompassed within the spirit and scope of the invention. Accordingly, the invention is limited only by the following claims.

What is claimed is:

1. A method comprising:
   a) isolating unlabeled Tau protein from a sample;
   b) obtaining unlabeled Tau protein fragments from the unlabeled Tau protein; and
   c) measuring the amount of at least two unlabeled Tau protein fragments by relating the ratio of a stable isotope-labeled Tau protein fragments quantitation internal standard to each of the at least two unlabeled Tau protein fragments, wherein:
   i) one of the at least two unlabeled Tau protein fragments is selected from the group consisting of SEQ ID NOs: 54, 74, 92 and 102; and
   ii) another of the at least two unlabeled Tau protein fragments is selected from the group consisting of SEQ ID NOs: 49-53, 55-91, 93-101 and 103-106.

2. The method of claim 1, wherein the sample is a cerebrospinal fluid (CSF), blood or plasma sample.

3. The method of claim 1, wherein the isotope is selected from the group consisting of 2H, 13C, 15N, 17O, 18O, 33S, 34S, and 36S.

4. The method of claim 1, wherein the isotope labeled Tau protein is 15N labeled Tau.

5. The method of claim 1, wherein measuring comprises analysis via mass spectroscopy.

6. The method of claim 5, wherein obtaining the at least two unlabeled Tau protein fragments comprises digesting the unlabeled Tau protein in the sample with a digestion enzyme.

7. The method of claim 6, wherein the digestion enzyme is trypsin.

8. The method of claim 6, wherein the digesting generates the at least two unlabeled Tau protein fragment having an amino acid sequence selected from the group consisting of SEQ ID NOs: 49-102.

* * * * *

SEQUENCE LISTING

<160> NUMBER OF SEQ ID NOS: 106

<210> SEQ ID NO 1
<211> LENGTH: 60
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly
    50                  55                  60

<210> SEQ ID NO 2
<211> LENGTH: 60
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly
    50                  55                  60

<210> SEQ ID NO 3
<211> LENGTH: 44
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys
        35                  40

<210> SEQ ID NO 4
<211> LENGTH: 60
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly
    50                  55                  60

<210> SEQ ID NO 5
<211> LENGTH: 60
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly
    50                  55                  60

<210> SEQ ID NO 6
<211> LENGTH: 44
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys
        35                  40

<210> SEQ ID NO 7
<211> LENGTH: 60
<212> TYPE: PRT

<213> ORGANISM: Homo sapiens

<400> SEQUENCE: 7

Ser Glu Thr Ser Asp Ala Lys Ser Thr Pro Thr Ala Glu Asp Val Thr
1               5                   10                  15
Ala Pro Leu Val Asp Glu Gly Ala Pro Gly Lys Gln Ala Ala Ala Gln
            20                  25                  30
Pro His Thr Glu Ile Pro Glu Gly Thr Thr Ala Glu Glu Ala Gly Ile
        35                  40                  45
Gly Asp Thr Pro Ser Leu Glu Asp Glu Ala Ala Gly
    50                  55                  60

<210> SEQ ID NO 8
<211> LENGTH: 31
<212> TYPE: PRT
<213> ORGANISM: Homo sapiens

<400> SEQUENCE: 8

Ser Glu Thr Ser Asp Ala Lys Ser Thr Pro Thr Ala Glu Ala Glu Glu
1               5                   10                  15
Ala Gly Ile Gly Asp Thr Pro Ser Leu Glu Asp Glu Ala Ala Gly
            20                  25                  30

<210> SEQ ID NO 9
<211> LENGTH: 18
<212> TYPE: PRT
<213> ORGANISM: Homo sapiens

<400> SEQUENCE: 9

Ala Glu Glu Ala Gly Ile Gly Asp Thr Pro Ser Leu Glu Asp Glu Ala
1               5                   10                  15
Ala Gly

<210> SEQ ID NO 10
<211> LENGTH: 60
<212> TYPE: PRT
<213> ORGANISM: Homo sapiens

<400> SEQUENCE: 10

Ser Glu Thr Ser Asp Ala Lys Ser Thr Pro Thr Ala Glu Asp Val Thr
1               5                   10                  15
Ala Pro Leu Val Asp Glu Gly Ala Pro Gly Lys Gln Ala Ala Ala Gln
            20                  25                  30
Pro His Thr Glu Ile Pro Glu Gly Thr Thr Ala Glu Glu Ala Gly Ile
        35                  40                  45
Gly Asp Thr Pro Ser Leu Glu Asp Glu Ala Ala Gly
    50                  55                  60

<210> SEQ ID NO 11
<211> LENGTH: 31
<212> TYPE: PRT
<213> ORGANISM: Homo sapiens

<400> SEQUENCE: 11

Ser Glu Thr Ser Asp Ala Lys Ser Thr Pro Thr Ala Glu Ala Glu Glu
1               5                   10                  15
Ala Gly Ile Gly Asp Thr Pro Ser Leu Glu Asp Glu Ala Ala Gly
            20                  25                  30

<210> SEQ ID NO 12

```
<211> LENGTH: 18
<212> TYPE: PRT
<213> ORGANISM: Homo sapiens

<400> SEQUENCE: 12

Ala Glu Glu Ala Gly Ile Gly Asp Thr Pro Ser Leu Glu Asp Glu Ala
1               5                   10                  15

Ala Gly

<210> SEQ ID NO 13
<211> LENGTH: 60
<212> TYPE: PRT
<213> ORGANISM: Homo sapiens

<400> SEQUENCE: 13

His Val Thr Gln Ala Arg Met Val Ser Lys Ser Lys Asp Gly Thr Gly
1               5                   10                  15

Ser Asp Asp Lys Lys Ala Lys Gly Ala Asp Gly Lys Thr Lys Ile Ala
                20                  25                  30

Thr Pro Arg Gly Ala Ala Pro Pro Gly Gln Lys Gly Gln Ala Asn Ala
            35                  40                  45

Thr Arg Ile Pro Ala Lys Thr Pro Pro Ala Pro Lys
        50                  55                  60

<210> SEQ ID NO 14
<211> LENGTH: 60
<212> TYPE: PRT
<213> ORGANISM: Homo sapiens

<400> SEQUENCE: 14

His Val Thr Gln Ala Arg Met Val Ser Lys Ser Lys Asp Gly Thr Gly
1               5                   10                  15

Ser Asp Asp Lys Lys Ala Lys Gly Ala Asp Gly Lys Thr Lys Ile Ala
                20                  25                  30

Thr Pro Arg Gly Ala Ala Pro Pro Gly Gln Lys Gly Gln Ala Asn Ala
            35                  40                  45

Thr Arg Ile Pro Ala Lys Thr Pro Pro Ala Pro Lys
        50                  55                  60

<210> SEQ ID NO 15
<211> LENGTH: 60
<212> TYPE: PRT
<213> ORGANISM: Homo sapiens

<400> SEQUENCE: 15

His Val Thr Gln Ala Arg Met Val Ser Lys Ser Lys Asp Gly Thr Gly
1               5                   10                  15

Ser Asp Asp Lys Lys Ala Lys Gly Ala Asp Gly Lys Thr Lys Ile Ala
                20                  25                  30

Thr Pro Arg Gly Ala Ala Pro Pro Gly Gln Lys Gly Gln Ala Asn Ala
            35                  40                  45

Thr Arg Ile Pro Ala Lys Thr Pro Pro Ala Pro Lys
        50                  55                  60

<210> SEQ ID NO 16
<211> LENGTH: 60
<212> TYPE: PRT
<213> ORGANISM: Homo sapiens

<400> SEQUENCE: 16
```

```
His Val Thr Gln Ala Arg Met Val Ser Lys Ser Lys Asp Gly Thr Gly
1               5                   10                  15

Ser Asp Asp Lys Lys Ala Lys Gly Ala Asp Gly Lys Thr Lys Ile Ala
                20                  25                  30

Thr Pro Arg Gly Ala Ala Pro Pro Gly Gln Lys Gly Gln Ala Asn Ala
            35                  40                  45

Thr Arg Ile Pro Ala Lys Thr Pro Pro Ala Pro Lys
50                  55                  60
```

<210> SEQ ID NO 17
<211> LENGTH: 60
<212> TYPE: PRT
<213> ORGANISM: Homo sapiens

<400> SEQUENCE: 17

```
His Val Thr Gln Ala Arg Met Val Ser Lys Ser Lys Asp Gly Thr Gly
1               5                   10                  15

Ser Asp Asp Lys Lys Ala Lys Gly Ala Asp Gly Lys Thr Lys Ile Ala
                20                  25                  30

Thr Pro Arg Gly Ala Ala Pro Pro Gly Gln Lys Gly Gln Ala Asn Ala
            35                  40                  45

Thr Arg Ile Pro Ala Lys Thr Pro Pro Ala Pro Lys
50                  55                  60
```

<210> SEQ ID NO 18
<211> LENGTH: 60
<212> TYPE: PRT
<213> ORGANISM: Homo sapiens

<400> SEQUENCE: 18

```
His Val Thr Gln Ala Arg Met Val Ser Lys Ser Lys Asp Gly Thr Gly
1               5                   10                  15

Ser Asp Asp Lys Lys Ala Lys Gly Ala Asp Gly Lys Thr Lys Ile Ala
                20                  25                  30

Thr Pro Arg Gly Ala Ala Pro Pro Gly Gln Lys Gly Gln Ala Asn Ala
            35                  40                  45

Thr Arg Ile Pro Ala Lys Thr Pro Pro Ala Pro Lys
50                  55                  60
```

<210> SEQ ID NO 19
<211> LENGTH: 60
<212> TYPE: PRT
<213> ORGANISM: Homo sapiens

<400> SEQUENCE: 19

```
Thr Pro Pro Ser Ser Gly Glu Pro Pro Lys Ser Gly Asp Arg Ser Gly
1               5                   10                  15

Tyr Ser Ser Pro Gly Ser Pro Gly Thr Pro Gly Ser Arg Ser Arg Thr
                20                  25                  30

Pro Ser Leu Pro Thr Pro Pro Thr Arg Glu Pro Lys Lys Val Ala Val
            35                  40                  45

Val Arg Thr Pro Pro Lys Ser Pro Ser Ser Ala Lys
50                  55                  60
```

<210> SEQ ID NO 20
<211> LENGTH: 60
<212> TYPE: PRT
<213> ORGANISM: Homo sapiens

<400> SEQUENCE: 20

```
Thr Pro Pro Ser Ser Gly Glu Pro Pro Lys Ser Gly Asp Arg Ser Gly
1               5                   10                  15

Tyr Ser Ser Pro Gly Ser Pro Gly Thr Pro Gly Ser Arg Ser Arg Thr
            20                  25                  30

Pro Ser Leu Pro Thr Pro Pro Thr Arg Glu Pro Lys Lys Val Ala Val
        35                  40                  45

Val Arg Thr Pro Pro Lys Ser Pro Ser Ser Ala Lys
    50                  55                  60
```

<210> SEQ ID NO 21
<211> LENGTH: 60
<212> TYPE: PRT
<213> ORGANISM: Homo sapiens

<400> SEQUENCE: 21

```
Thr Pro Pro Ser Ser Gly Glu Pro Pro Lys Ser Gly Asp Arg Ser Gly
1               5                   10                  15

Tyr Ser Ser Pro Gly Ser Pro Gly Thr Pro Gly Ser Arg Ser Arg Thr
            20                  25                  30

Pro Ser Leu Pro Thr Pro Pro Thr Arg Glu Pro Lys Lys Val Ala Val
        35                  40                  45

Val Arg Thr Pro Pro Lys Ser Pro Ser Ser Ala Lys
    50                  55                  60
```

<210> SEQ ID NO 22
<211> LENGTH: 60
<212> TYPE: PRT
<213> ORGANISM: Homo sapiens

<400> SEQUENCE: 22

```
Thr Pro Pro Ser Ser Gly Glu Pro Pro Lys Ser Gly Asp Arg Ser Gly
1               5                   10                  15

Tyr Ser Ser Pro Gly Ser Pro Gly Thr Pro Gly Ser Arg Ser Arg Thr
            20                  25                  30

Pro Ser Leu Pro Thr Pro Pro Thr Arg Glu Pro Lys Lys Val Ala Val
        35                  40                  45

Val Arg Thr Pro Pro Lys Ser Pro Ser Ser Ala Lys
    50                  55                  60
```

<210> SEQ ID NO 23
<211> LENGTH: 60
<212> TYPE: PRT
<213> ORGANISM: Homo sapiens

<400> SEQUENCE: 23

```
Thr Pro Pro Ser Ser Gly Glu Pro Pro Lys Ser Gly Asp Arg Ser Gly
1               5                   10                  15

Tyr Ser Ser Pro Gly Ser Pro Gly Thr Pro Gly Ser Arg Ser Arg Thr
            20                  25                  30

Pro Ser Leu Pro Thr Pro Pro Thr Arg Glu Pro Lys Lys Val Ala Val
        35                  40                  45

Val Arg Thr Pro Pro Lys Ser Pro Ser Ser Ala Lys
    50                  55                  60
```

<210> SEQ ID NO 24
<211> LENGTH: 60
<212> TYPE: PRT
<213> ORGANISM: Homo sapiens

```
<400> SEQUENCE: 24

Thr Pro Pro Ser Ser Gly Glu Pro Pro Lys Ser Gly Asp Arg Ser Gly
1               5                   10                  15

Tyr Ser Ser Pro Gly Ser Pro Gly Thr Pro Gly Ser Arg Ser Arg Thr
            20                  25                  30

Pro Ser Leu Pro Thr Pro Thr Arg Glu Pro Lys Lys Val Ala Val
        35                  40                  45

Val Arg Thr Pro Pro Lys Ser Pro Ser Ser Ala Lys
50                  55                  60

<210> SEQ ID NO 25
<211> LENGTH: 60
<212> TYPE: PRT
<213> ORGANISM: Homo sapiens

<400> SEQUENCE: 25

Ser Arg Leu Gln Thr Ala Pro Val Pro Met Pro Asp Leu Lys Asn Val
1               5                   10                  15

Lys Ser Lys Ile Gly Ser Thr Glu Asn Leu Lys His Gln Pro Gly Gly
            20                  25                  30

Gly Lys Val Gln Ile Ile Asn Lys Lys Leu Asp Leu Ser Asn Val Gln
        35                  40                  45

Ser Lys Cys Gly Ser Lys Asp Asn Ile Lys His Val
50                  55                  60

<210> SEQ ID NO 26
<211> LENGTH: 60
<212> TYPE: PRT
<213> ORGANISM: Homo sapiens

<400> SEQUENCE: 26

Ser Arg Leu Gln Thr Ala Pro Val Pro Met Pro Asp Leu Lys Asn Val
1               5                   10                  15

Lys Ser Lys Ile Gly Ser Thr Glu Asn Leu Lys His Gln Pro Gly Gly
            20                  25                  30

Gly Lys Val Gln Ile Ile Asn Lys Lys Leu Asp Leu Ser Asn Val Gln
        35                  40                  45

Ser Lys Cys Gly Ser Lys Asp Asn Ile Lys His Val
50                  55                  60

<210> SEQ ID NO 27
<211> LENGTH: 60
<212> TYPE: PRT
<213> ORGANISM: Homo sapiens

<400> SEQUENCE: 27

Ser Arg Leu Gln Thr Ala Pro Val Pro Met Pro Asp Leu Lys Asn Val
1               5                   10                  15

Lys Ser Lys Ile Gly Ser Thr Glu Asn Leu Lys His Gln Pro Gly Gly
            20                  25                  30

Gly Lys Val Gln Ile Ile Asn Lys Lys Leu Asp Leu Ser Asn Val Gln
        35                  40                  45

Ser Lys Cys Gly Ser Lys Asp Asn Ile Lys His Val
50                  55                  60

<210> SEQ ID NO 28
<211> LENGTH: 34
<212> TYPE: PRT
<213> ORGANISM: Homo sapiens
```

<400> SEQUENCE: 28

Ser Arg Leu Gln Thr Ala Pro Val Pro Met Pro Asp Leu Lys Asn Val
1               5                   10                  15

Lys Ser Lys Ile Gly Ser Thr Glu Asn Leu Lys His Gln Pro Gly Gly
            20                  25                  30

Gly Lys

<210> SEQ ID NO 29
<211> LENGTH: 34
<212> TYPE: PRT
<213> ORGANISM: Homo sapiens

<400> SEQUENCE: 29

Ser Arg Leu Gln Thr Ala Pro Val Pro Met Pro Asp Leu Lys Asn Val
1               5                   10                  15

Lys Ser Lys Ile Gly Ser Thr Glu Asn Leu Lys His Gln Pro Gly Gly
            20                  25                  30

Gly Lys

<210> SEQ ID NO 30
<211> LENGTH: 34
<212> TYPE: PRT
<213> ORGANISM: Homo sapiens

<400> SEQUENCE: 30

Ser Arg Leu Gln Thr Ala Pro Val Pro Met Pro Asp Leu Lys Asn Val
1               5                   10                  15

Lys Ser Lys Ile Gly Ser Thr Glu Asn Leu Lys His Gln Pro Gly Gly
            20                  25                  30

Gly Lys

<210> SEQ ID NO 31
<211> LENGTH: 60
<212> TYPE: PRT
<213> ORGANISM: Homo sapiens

<400> SEQUENCE: 31

Pro Gly Gly Gly Ser Val Gln Ile Val Tyr Lys Pro Val Asp Leu Ser
1               5                   10                  15

Lys Val Thr Ser Lys Cys Gly Ser Leu Gly Asn Ile His His Lys Pro
            20                  25                  30

Gly Gly Gly Gln Val Glu Val Lys Ser Glu Lys Leu Asp Phe Lys Asp
        35                  40                  45

Arg Val Gln Ser Lys Ile Gly Ser Leu Asp Asn Ile
    50                  55                  60

<210> SEQ ID NO 32
<211> LENGTH: 60
<212> TYPE: PRT
<213> ORGANISM: Homo sapiens

<400> SEQUENCE: 32

Pro Gly Gly Gly Ser Val Gln Ile Val Tyr Lys Pro Val Asp Leu Ser
1               5                   10                  15

Lys Val Thr Ser Lys Cys Gly Ser Leu Gly Asn Ile His His Lys Pro
            20                  25                  30

Gly Gly Gly Gln Val Glu Val Lys Ser Glu Lys Leu Asp Phe Lys Asp
        35                  40                  45

```
Arg Val Gln Ser Lys Ile Gly Ser Leu Asp Asn Ile
 50                  55                  60
```

<210> SEQ ID NO 33
<211> LENGTH: 60
<212> TYPE: PRT
<213> ORGANISM: Homo sapiens

<400> SEQUENCE: 33

```
Pro Gly Gly Gly Ser Val Gln Ile Val Tyr Lys Pro Val Asp Leu Ser
 1               5                  10                  15

Lys Val Thr Ser Lys Cys Gly Ser Leu Gly Asn Ile His His Lys Pro
             20                  25                  30

Gly Gly Gly Gln Val Glu Val Lys Ser Glu Lys Leu Asp Phe Lys Asp
         35                  40                  45

Arg Val Gln Ser Lys Ile Gly Ser Leu Asp Asn Ile
 50                  55                  60
```

<210> SEQ ID NO 34
<211> LENGTH: 55
<212> TYPE: PRT
<213> ORGANISM: Homo sapiens

<400> SEQUENCE: 34

```
Val Gln Ile Val Tyr Lys Pro Val Asp Leu Ser Lys Val Thr Ser Lys
 1               5                  10                  15

Cys Gly Ser Leu Gly Asn Ile His His Lys Pro Gly Gly Gly Gln Val
             20                  25                  30

Glu Val Lys Ser Glu Lys Leu Asp Phe Lys Asp Arg Val Gln Ser Lys
         35                  40                  45

Ile Gly Ser Leu Asp Asn Ile
 50                  55
```

<210> SEQ ID NO 35
<211> LENGTH: 55
<212> TYPE: PRT
<213> ORGANISM: Homo sapiens

<400> SEQUENCE: 35

```
Val Gln Ile Val Tyr Lys Pro Val Asp Leu Ser Lys Val Thr Ser Lys
 1               5                  10                  15

Cys Gly Ser Leu Gly Asn Ile His His Lys Pro Gly Gly Gly Gln Val
             20                  25                  30

Glu Val Lys Ser Glu Lys Leu Asp Phe Lys Asp Arg Val Gln Ser Lys
         35                  40                  45

Ile Gly Ser Leu Asp Asn Ile
 50                  55
```

<210> SEQ ID NO 36
<211> LENGTH: 55
<212> TYPE: PRT
<213> ORGANISM: Homo sapiens

<400> SEQUENCE: 36

```
Val Gln Ile Val Tyr Lys Pro Val Asp Leu Ser Lys Val Thr Ser Lys
 1               5                  10                  15

Cys Gly Ser Leu Gly Asn Ile His His Lys Pro Gly Gly Gly Gln Val
             20                  25                  30

Glu Val Lys Ser Glu Lys Leu Asp Phe Lys Asp Arg Val Gln Ser Lys
```

```
                35                  40                  45

Ile Gly Ser Leu Asp Asn Ile
    50                  55

<210> SEQ ID NO 37
<211> LENGTH: 60
<212> TYPE: PRT
<213> ORGANISM: Homo sapiens

<400> SEQUENCE: 37

Thr His Val Pro Gly Gly Gly Asn Lys Lys Ile Glu Thr His Lys Leu
1               5                   10                  15

Thr Phe Arg Glu Asn Ala Lys Ala Lys Thr Asp His Gly Ala Glu Ile
            20                  25                  30

Val Tyr Lys Ser Pro Val Val Ser Gly Asp Thr Ser Pro Arg His Leu
        35                  40                  45

Ser Asn Val Ser Ser Thr Gly Ser Ile Asp Met Val
    50                  55                  60

<210> SEQ ID NO 38
<211> LENGTH: 60
<212> TYPE: PRT
<213> ORGANISM: Homo sapiens

<400> SEQUENCE: 38

Thr His Val Pro Gly Gly Gly Asn Lys Lys Ile Glu Thr His Lys Leu
1               5                   10                  15

Thr Phe Arg Glu Asn Ala Lys Ala Lys Thr Asp His Gly Ala Glu Ile
            20                  25                  30

Val Tyr Lys Ser Pro Val Val Ser Gly Asp Thr Ser Pro Arg His Leu
        35                  40                  45

Ser Asn Val Ser Ser Thr Gly Ser Ile Asp Met Val
    50                  55                  60

<210> SEQ ID NO 39
<211> LENGTH: 60
<212> TYPE: PRT
<213> ORGANISM: Homo sapiens

<400> SEQUENCE: 39

Thr His Val Pro Gly Gly Gly Asn Lys Lys Ile Glu Thr His Lys Leu
1               5                   10                  15

Thr Phe Arg Glu Asn Ala Lys Ala Lys Thr Asp His Gly Ala Glu Ile
            20                  25                  30

Val Tyr Lys Ser Pro Val Val Ser Gly Asp Thr Ser Pro Arg His Leu
        35                  40                  45

Ser Asn Val Ser Ser Thr Gly Ser Ile Asp Met Val
    50                  55                  60

<210> SEQ ID NO 40
<211> LENGTH: 60
<212> TYPE: PRT
<213> ORGANISM: Homo sapiens

<400> SEQUENCE: 40

Thr His Val Pro Gly Gly Gly Asn Lys Lys Ile Glu Thr His Lys Leu
1               5                   10                  15

Thr Phe Arg Glu Asn Ala Lys Ala Lys Thr Asp His Gly Ala Glu Ile
            20                  25                  30
```

Val Tyr Lys Ser Pro Val Val Ser Gly Asp Thr Ser Pro Arg His Leu
            35                  40                  45

Ser Asn Val Ser Ser Thr Gly Ser Ile Asp Met Val
    50                  55                  60

<210> SEQ ID NO 41
<211> LENGTH: 60
<212> TYPE: PRT
<213> ORGANISM: Homo sapiens

<400> SEQUENCE: 41

Thr His Val Pro Gly Gly Gly Asn Lys Lys Ile Glu Thr His Lys Leu
1               5                   10                  15

Thr Phe Arg Glu Asn Ala Lys Ala Lys Thr Asp His Gly Ala Glu Ile
            20                  25                  30

Val Tyr Lys Ser Pro Val Val Ser Gly Asp Thr Ser Pro Arg His Leu
            35                  40                  45

Ser Asn Val Ser Ser Thr Gly Ser Ile Asp Met Val
    50                  55                  60

<210> SEQ ID NO 42
<211> LENGTH: 60
<212> TYPE: PRT
<213> ORGANISM: Homo sapiens

<400> SEQUENCE: 42

Thr His Val Pro Gly Gly Gly Asn Lys Lys Ile Glu Thr His Lys Leu
1               5                   10                  15

Thr Phe Arg Glu Asn Ala Lys Ala Lys Thr Asp His Gly Ala Glu Ile
            20                  25                  30

Val Tyr Lys Ser Pro Val Val Ser Gly Asp Thr Ser Pro Arg His Leu
            35                  40                  45

Ser Asn Val Ser Ser Thr Gly Ser Ile Asp Met Val
    50                  55                  60

<210> SEQ ID NO 43
<211> LENGTH: 21
<212> TYPE: PRT
<213> ORGANISM: Homo sapiens

<400> SEQUENCE: 43

Asp Ser Pro Gln Leu Ala Thr Leu Ala Asp Glu Val Ser Ala Ser Leu
1               5                   10                  15

Ala Lys Gln Gly Leu
            20

<210> SEQ ID NO 44
<211> LENGTH: 21
<212> TYPE: PRT
<213> ORGANISM: Homo sapiens

<400> SEQUENCE: 44

Asp Ser Pro Gln Leu Ala Thr Leu Ala Asp Glu Val Ser Ala Ser Leu
1               5                   10                  15

Ala Lys Gln Gly Leu
            20

<210> SEQ ID NO 45
<211> LENGTH: 21
<212> TYPE: PRT
<213> ORGANISM: Homo sapiens

<400> SEQUENCE: 45

Asp Ser Pro Gln Leu Ala Thr Leu Ala Asp Glu Val Ser Ala Ser Leu
1               5                   10                  15

Ala Lys Gln Gly Leu
            20

<210> SEQ ID NO 46
<211> LENGTH: 21
<212> TYPE: PRT
<213> ORGANISM: Homo sapiens

<400> SEQUENCE: 46

Asp Ser Pro Gln Leu Ala Thr Leu Ala Asp Glu Val Ser Ala Ser Leu
1               5                   10                  15

Ala Lys Gln Gly Leu
            20

<210> SEQ ID NO 47
<211> LENGTH: 21
<212> TYPE: PRT
<213> ORGANISM: Homo sapiens

<400> SEQUENCE: 47

Asp Ser Pro Gln Leu Ala Thr Leu Ala Asp Glu Val Ser Ala Ser Leu
1               5                   10                  15

Ala Lys Gln Gly Leu
            20

<210> SEQ ID NO 48
<211> LENGTH: 21
<212> TYPE: PRT
<213> ORGANISM: Homo sapiens

<400> SEQUENCE: 48

Asp Ser Pro Gln Leu Ala Thr Leu Ala Asp Glu Val Ser Ala Ser Leu
1               5                   10                  15

Ala Lys Gln Gly Leu
            20

<210> SEQ ID NO 49
<211> LENGTH: 20
<212> TYPE: PRT
<213> ORGANISM: Homo sapiens

<400> SEQUENCE: 49

Arg Gln Glu Phe Glu Val Met Glu Asp His Ala Gly Thr Tyr Gly Leu
1               5                   10                  15

Gly Asp Arg Lys
            20

<210> SEQ ID NO 50
<211> LENGTH: 23
<212> TYPE: PRT
<213> ORGANISM: Homo sapiens

<400> SEQUENCE: 50

Arg Lys Asp Gln Gly Gly Tyr Thr Met His Gln Asp Gln Glu Gly Asp
1               5                   10                  15

Thr Asp Ala Gly Leu Lys Glu
            20

<210> SEQ ID NO 51
<211> LENGTH: 25
<212> TYPE: PRT
<213> ORGANISM: Homo sapiens

<400> SEQUENCE: 51

Lys Glu Ser Pro Leu Gln Thr Pro Thr Glu Asp Gly Ser Glu Glu Pro
1               5                   10                  15

Gly Ser Glu Thr Ser Asp Ala Lys Ser
            20                  25

<210> SEQ ID NO 52
<211> LENGTH: 22
<212> TYPE: PRT
<213> ORGANISM: Homo sapiens

<400> SEQUENCE: 52

Lys Ser Thr Pro Thr Ala Glu Asp Val Thr Ala Pro Leu Val Asp Glu
1               5                   10                  15

Gly Ala Pro Gly Lys Gln
            20

<210> SEQ ID NO 53
<211> LENGTH: 41
<212> TYPE: PRT
<213> ORGANISM: Homo sapiens

<400> SEQUENCE: 53

Lys Gln Ala Ala Ala Gln Pro His Thr Glu Ile Pro Glu Gly Thr Thr
1               5                   10                  15

Ala Glu Glu Ala Gly Ile Gly Asp Thr Pro Ser Leu Glu Asp Glu Ala
            20                  25                  30

Ala Gly His Val Thr Gln Ala Arg Met
            35                  40

<210> SEQ ID NO 54
<211> LENGTH: 7
<212> TYPE: PRT
<213> ORGANISM: Homo sapiens

<400> SEQUENCE: 54

Lys Ile Ala Thr Pro Arg Gly
1               5

<210> SEQ ID NO 55
<211> LENGTH: 10
<212> TYPE: PRT
<213> ORGANISM: Homo sapiens

<400> SEQUENCE: 55

Arg Gly Ala Ala Pro Pro Gly Gln Lys Gly
1               5                   10

<210> SEQ ID NO 56
<211> LENGTH: 8
<212> TYPE: PRT
<213> ORGANISM: Homo sapiens

<400> SEQUENCE: 56

Lys Thr Pro Pro Ala Pro Lys Thr
1               5

```
<210> SEQ ID NO 57
<211> LENGTH: 12
<212> TYPE: PRT
<213> ORGANISM: Homo sapiens

<400> SEQUENCE: 57

Lys Thr Pro Pro Ser Ser Gly Glu Pro Pro Lys Ser
1               5                   10

<210> SEQ ID NO 58
<211> LENGTH: 17
<212> TYPE: PRT
<213> ORGANISM: Homo sapiens

<400> SEQUENCE: 58

Arg Ser Gly Tyr Ser Ser Pro Gly Ser Pro Gly Thr Pro Gly Ser Arg
1               5                   10                  15

Ser

<210> SEQ ID NO 59
<211> LENGTH: 12
<212> TYPE: PRT
<213> ORGANISM: Homo sapiens

<400> SEQUENCE: 59

Arg Thr Pro Ser Leu Pro Thr Pro Pro Thr Arg Glu
1               5                   10

<210> SEQ ID NO 60
<211> LENGTH: 15
<212> TYPE: PRT
<213> ORGANISM: Homo sapiens

<400> SEQUENCE: 60

Arg Thr Pro Ser Leu Pro Thr Pro Pro Thr Arg Glu Pro Lys Lys
1               5                   10                  15

<210> SEQ ID NO 61
<211> LENGTH: 10
<212> TYPE: PRT
<213> ORGANISM: Homo sapiens

<400> SEQUENCE: 61

Lys Ile Gly Ser Thr Glu Asn Leu Lys His
1               5                   10

<210> SEQ ID NO 62
<211> LENGTH: 8
<212> TYPE: PRT
<213> ORGANISM: Homo sapiens

<400> SEQUENCE: 62

Lys Val Gln Ile Ile Asn Lys Lys
1               5

<210> SEQ ID NO 63
<211> LENGTH: 14
<212> TYPE: PRT
<213> ORGANISM: Homo sapiens

<400> SEQUENCE: 63

Lys Val Gln Ile Val Tyr Lys Pro Val Asp Leu Ser Lys Val
1               5                   10
```

```
<210> SEQ ID NO 64
<211> LENGTH: 11
<212> TYPE: PRT
<213> ORGANISM: Homo sapiens

<400> SEQUENCE: 64

Lys Leu Asp Leu Ser Asn Val Gln Ser Lys Cys
1               5                   10

<210> SEQ ID NO 65
<211> LENGTH: 21
<212> TYPE: PRT
<213> ORGANISM: Homo sapiens

<400> SEQUENCE: 65

Lys His Val Pro Gly Gly Gly Ser Val Gln Ile Val Tyr Lys Pro Val
1               5                   10                  15

Asp Leu Ser Lys Val
            20

<210> SEQ ID NO 66
<211> LENGTH: 18
<212> TYPE: PRT
<213> ORGANISM: Homo sapiens

<400> SEQUENCE: 66

Lys Ile Gly Ser Leu Asp Asn Ile Thr His Val Pro Gly Gly Gly Asn
1               5                   10                  15

Lys Lys

<210> SEQ ID NO 67
<211> LENGTH: 12
<212> TYPE: PRT
<213> ORGANISM: Homo sapiens

<400> SEQUENCE: 67

Lys Thr Asp His Gly Ala Glu Ile Val Tyr Lys Ser
1               5                   10

<210> SEQ ID NO 68
<211> LENGTH: 13
<212> TYPE: PRT
<213> ORGANISM: Homo sapiens

<400> SEQUENCE: 68

Lys Ser Pro Val Val Ser Gly Asp Thr Ser Pro Arg His
1               5                   10

<210> SEQ ID NO 69
<211> LENGTH: 18
<212> TYPE: PRT
<213> ORGANISM: Homo sapiens

<400> SEQUENCE: 69

Gln Glu Phe Glu Val Met Glu Asp His Ala Gly Thr Tyr His Leu His
1               5                   10                  15

Asp Arg

<210> SEQ ID NO 70
<211> LENGTH: 21
<212> TYPE: PRT
<213> ORGANISM: Homo sapiens

<400> SEQUENCE: 70
```

Lys Asp Gln Gly Gly Tyr Thr Met His Gln Asp Gln Glu Gly Asp Thr
1               5                   10                  15

Asp Ala Gly Leu Lys
            20

<210> SEQ ID NO 71
<211> LENGTH: 23
<212> TYPE: PRT
<213> ORGANISM: Homo sapiens

<400> SEQUENCE: 71

Glu Ser Pro Leu Gln Thr Pro Thr Glu Asp Phe Ser Glu Glu Pro Gly
1               5                   10                  15

Ser Glu Thr Ser Asp Ala Lys
            20

<210> SEQ ID NO 72
<211> LENGTH: 20
<212> TYPE: PRT
<213> ORGANISM: Homo sapiens

<400> SEQUENCE: 72

Ser Thr Pro Thr Ala Glu Asp Val Thr Ala Pro Leu Val Asp Glu Gly
1               5                   10                  15

Ala Pro Gly Lys
            20

<210> SEQ ID NO 73
<211> LENGTH: 39
<212> TYPE: PRT
<213> ORGANISM: Homo sapiens

<400> SEQUENCE: 73

Gln Ala Ala Ala Gln Pro His Thr Glu Ile Pro Glu Gly Thr Thr Ala
1               5                   10                  15

Glu Glu Ala Gly Ile Gly Asp Thr Pro Ser Leu Glu Asp Glu Ala Ala
            20                  25                  30

Gly His Val Thr Gln Ala Arg
        35

<210> SEQ ID NO 74
<211> LENGTH: 5
<212> TYPE: PRT
<213> ORGANISM: Homo sapiens

<400> SEQUENCE: 74

Ile Ala Thr Pro Arg
1               5

<210> SEQ ID NO 75
<211> LENGTH: 6
<212> TYPE: PRT
<213> ORGANISM: Homo sapiens

<400> SEQUENCE: 75

Thr Pro Pro Ala Pro Lys
1               5

<210> SEQ ID NO 76
<211> LENGTH: 10
<212> TYPE: PRT
<213> ORGANISM: Homo sapiens

<400> SEQUENCE: 76

Thr Pro Pro Ser Ser Gly Glu Pro Pro Lys
1               5                   10

<210> SEQ ID NO 77
<211> LENGTH: 15
<212> TYPE: PRT
<213> ORGANISM: Homo sapiens

<400> SEQUENCE: 77

Ser Gly Tyr Ser Ser Pro Gly Ser Pro Gly Thr Pro Gly Ser Arg
1               5                   10                  15

<210> SEQ ID NO 78
<211> LENGTH: 10
<212> TYPE: PRT
<213> ORGANISM: Homo sapiens

<400> SEQUENCE: 78

Thr Pro Ser Leu Pro Thr Pro Pro Thr Arg
1               5                   10

<210> SEQ ID NO 79
<211> LENGTH: 13
<212> TYPE: PRT
<213> ORGANISM: Homo sapiens

<400> SEQUENCE: 79

Thr Pro Ser Leu Pro Thr Pro Pro Thr Arg Glu Pro Lys
1               5                   10

<210> SEQ ID NO 80
<211> LENGTH: 8
<212> TYPE: PRT
<213> ORGANISM: Homo sapiens

<400> SEQUENCE: 80

Ile Gly Ser Thr Glu Asn Leu Lys
1               5

<210> SEQ ID NO 81
<211> LENGTH: 6
<212> TYPE: PRT
<213> ORGANISM: Homo sapiens

<400> SEQUENCE: 81

Val Gln Ile Ile Asn Lys
1               5

<210> SEQ ID NO 82
<211> LENGTH: 9
<212> TYPE: PRT
<213> ORGANISM: Homo sapiens

<400> SEQUENCE: 82

Leu Asp Leu Ser Asn Val Trp Ser Lys
1               5

<210> SEQ ID NO 83
<211> LENGTH: 19
<212> TYPE: PRT
<213> ORGANISM: Homo sapiens

<400> SEQUENCE: 83

His Val Pro Gly Gly Ser Val Gln Ile Cys Tyr Lys Pro Val Asp
1               5                   10                  15

Leu Ser Lys

<210> SEQ ID NO 84
<211> LENGTH: 16
<212> TYPE: PRT
<213> ORGANISM: Homo sapiens

<400> SEQUENCE: 84

Ile Gly Ser Leu Asp Asn Ile Thr His Val Pro Gly Gly Asn Lys
1               5                   10                  15

<210> SEQ ID NO 85
<211> LENGTH: 10
<212> TYPE: PRT
<213> ORGANISM: Homo sapiens

<400> SEQUENCE: 85

Thr Asp His Gly Ala Glu Ile Val Tyr Lys
1               5                   10

<210> SEQ ID NO 86
<211> LENGTH: 11
<212> TYPE: PRT
<213> ORGANISM: Homo sapiens

<400> SEQUENCE: 86

Ser Pro Val Val Ser Gly Asp Thr Ser Pro Arg
1               5                   10

<210> SEQ ID NO 87
<211> LENGTH: 18
<212> TYPE: PRT
<213> ORGANISM: Homo sapiens

<400> SEQUENCE: 87

Gln Glu Phe Glu Val Met Glu Asp His Ala Gly Thr Tyr His Leu His
1               5                   10                  15

Asp Arg

<210> SEQ ID NO 88
<211> LENGTH: 21
<212> TYPE: PRT
<213> ORGANISM: Homo sapiens

<400> SEQUENCE: 88

Lys Asp Gln Gly Gly Tyr Thr Met His Gln Asp Gln Glu Gly Asp Thr
1               5                   10                  15

Asp Ala Gly Leu Lys
            20

<210> SEQ ID NO 89
<211> LENGTH: 23
<212> TYPE: PRT
<213> ORGANISM: Homo sapiens

<400> SEQUENCE: 89

Glu Ser Pro Leu Gln Thr Pro Thr Glu Asp Phe Ser Glu Glu Pro Gly
1               5                   10                  15

Ser Glu Thr Ser Asp Ala Lys
            20

<210> SEQ ID NO 90
<211> LENGTH: 20
<212> TYPE: PRT
<213> ORGANISM: Homo sapiens

<400> SEQUENCE: 90

Ser Thr Pro Thr Ala Glu Asp Val Thr Ala Pro Leu Val Asp Glu Gly
1               5                   10                  15

Ala Pro Gly Lys
            20

<210> SEQ ID NO 91
<211> LENGTH: 37
<212> TYPE: PRT
<213> ORGANISM: Homo sapiens

<400> SEQUENCE: 91

Gln Ala Ala Ala Gln Pro His Thr Glu Ile Pro Glu Gly Thr Thr Ala
1               5                   10                  15

Glu Glu Ala Gly Ile Gly Asp Thr Pro Ser Leu Glu Asp Glu Ala Ala
                20                  25                  30

Gly His Val Thr Gln
            35

<210> SEQ ID NO 92
<211> LENGTH: 5
<212> TYPE: PRT
<213> ORGANISM: Homo sapiens

<400> SEQUENCE: 92

Ile Ala Thr Pro Arg
1               5

<210> SEQ ID NO 93
<211> LENGTH: 6
<212> TYPE: PRT
<213> ORGANISM: Homo sapiens

<400> SEQUENCE: 93

Thr Pro Pro Ala Pro Lys
1               5

<210> SEQ ID NO 94
<211> LENGTH: 10
<212> TYPE: PRT
<213> ORGANISM: Homo sapiens

<400> SEQUENCE: 94

Thr Pro Pro Ser Ser Gly Glu Pro Pro Lys
1               5                   10

<210> SEQ ID NO 95
<211> LENGTH: 15
<212> TYPE: PRT
<213> ORGANISM: Homo sapiens

<400> SEQUENCE: 95

Ser Gly Tyr Ser Ser Pro Gly Ser Pro Gly Thr Pro Gly Ser Arg
1               5                   10                  15

<210> SEQ ID NO 96
<211> LENGTH: 10

<212> TYPE: PRT
<213> ORGANISM: Homo sapiens

<400> SEQUENCE: 96

Thr Pro Ser Leu Pro Thr Pro Pro Thr Arg
1               5                   10

<210> SEQ ID NO 97
<211> LENGTH: 18
<212> TYPE: PRT
<213> ORGANISM: Homo sapiens

<400> SEQUENCE: 97

Gln Glu Phe Glu Val Met Glu Asp His Ala Gly Thr Tyr His Leu His
1               5                   10                  15

Asp Arg

<210> SEQ ID NO 98
<211> LENGTH: 21
<212> TYPE: PRT
<213> ORGANISM: Homo sapiens

<400> SEQUENCE: 98

Lys Asp Gln Gly Gly Tyr Thr Met His Gln Asp Gln Glu Gly Asp Thr
1               5                   10                  15

Asp Ala Gly Leu Lys
            20

<210> SEQ ID NO 99
<211> LENGTH: 23
<212> TYPE: PRT
<213> ORGANISM: Homo sapiens

<400> SEQUENCE: 99

Glu Ser Pro Leu Gln Thr Pro Thr Glu Asp Phe Ser Glu Glu Pro Gly
1               5                   10                  15

Ser Glu Thr Ser Asp Ala Lys
            20

<210> SEQ ID NO 100
<211> LENGTH: 20
<212> TYPE: PRT
<213> ORGANISM: Homo sapiens

<400> SEQUENCE: 100

Ser Thr Pro Thr Ala Glu Asp Val Thr Ala Pro Leu Val Asp Glu Gly
1               5                   10                  15

Ala Pro Gly Lys
            20

<210> SEQ ID NO 101
<211> LENGTH: 39
<212> TYPE: PRT
<213> ORGANISM: Homo sapiens

<400> SEQUENCE: 101

Gln Ala Ala Ala Gln Pro His Thr Glu Ile Pro Glu Gly Thr Thr Ala
1               5                   10                  15

Glu Glu Ala Gly Ile Gly Asp Thr Pro Ser Leu Glu Asp Glu Ala Ala
            20                  25                  30

Gly His Val Thr Gln Ala Arg
        35

```
<210> SEQ ID NO 102
<211> LENGTH: 5
<212> TYPE: PRT
<213> ORGANISM: Homo sapiens

<400> SEQUENCE: 102

Ile Ala Thr Pro Arg
1               5

<210> SEQ ID NO 103
<211> LENGTH: 6
<212> TYPE: PRT
<213> ORGANISM: Homo sapiens

<400> SEQUENCE: 103

Thr Pro Pro Ala Pro Lys
1               5

<210> SEQ ID NO 104
<211> LENGTH: 10
<212> TYPE: PRT
<213> ORGANISM: Homo sapiens

<400> SEQUENCE: 104

Thr Pro Pro Ser Ser Gly Glu Pro Pro Lys
1               5                   10

<210> SEQ ID NO 105
<211> LENGTH: 15
<212> TYPE: PRT
<213> ORGANISM: Homo sapiens

<400> SEQUENCE: 105

Ser Gly Tyr Ser Ser Pro Gly Ser Pro Gly Thr Pro Gly Ser Arg
1               5                   10                  15

<210> SEQ ID NO 106
<211> LENGTH: 10
<212> TYPE: PRT
<213> ORGANISM: Homo sapiens

<400> SEQUENCE: 106

Thr Pro Ser Leu Pro Thr Pro Pro Thr Arg
1               5                   10
```